(12) United States Patent
Graves et al.

(10) Patent No.: US 6,194,625 B1
(45) Date of Patent: Feb. 27, 2001

(54) ALKYLATION BY CONTROLLING OLEFIN RATIOS

(75) Inventors: David C. Graves; Ken Edward Kranz; James Kevin Millard, all of Kansas City, MO (US); Lyle Frederick Albright, West Lafayette, IN (US)

(73) Assignee: Stratco, Inc., Leawood, KS (US)

( * ) Notice: Subject to any disclaimer, the term of this patent is extended or adjusted under 35 U.S.C. 154(b) by 0 days.

(21) Appl. No.: 09/158,278

(22) Filed: Sep. 22, 1998

Related U.S. Application Data

(63) Continuation-in-part of application No. 08/911,219, filed on Aug. 15, 1997, now Pat. No. 5,841,014, which is a continuation of application No. 08/755,721, filed on Nov. 25, 1996, now abandoned, which is a continuation of application No. 08/315,926, filed on Sep. 30, 1994, now abandoned.

(51) Int. Cl.[7] .................. C07C 2/00; C07C 2/54; C07C 2/58; C07C 2/62

(52) U.S. Cl. .................. 585/313; 585/312; 585/331; 585/709; 585/716; 585/721; 585/723; 582/22; 582/29; 582/31

(58) Field of Search .................. 585/312, 313, 585/331, 709, 716, 721, 723; 502/22, 29, 31

(56) References Cited

U.S. PATENT DOCUMENTS

| | | | |
|---|---|---|---|
| 2,351,464 | * 6/1944 | Voorhies, Jr. et al. | 585/301 |
| 2,405,993 | * 8/1946 | Burk | 208/115 |
| 2,436,483 | * 2/1948 | Newman | 585/331 |
| 2,438,456 | * 3/1948 | Russell | 585/331 |
| 2,509,028 | * 5/1950 | Abrams et al. | 208/64 |
| 3,045,055 | * 7/1962 | Van Pool et al. | 208/141 |
| 3,211,803 | * 10/1965 | Chapman | 585/719 |
| 3,502,569 | * 3/1970 | Hervert | 208/49 |
| 3,683,041 | * 8/1972 | Goldsby | 585/331 |
| 3,778,489 | * 12/1973 | Parker et al. | 585/722 |
| 3,998,903 | * 12/1976 | Sobel | 585/716 |
| 4,225,740 | * 9/1980 | Chapman et al. | 585/719 |
| 5,648,586 | * 7/1997 | Sampath | 585/716 |
| 5,841,014 | * 11/1998 | Graves et al. | 585/313 |

* cited by examiner

Primary Examiner—Elizabeth D. Wood
(74) Attorney, Agent, or Firm—J. M. (Mark) Gilbreth; Gilbreth & Associates, P.C.

(57) ABSTRACT

Disclosed are various embodiments for alkylating olefins and isoparaffins in the presence of an acid to reduce and/or control acid consumption or maximize and/or control the octane number of the produced alkylate product. One embodiment includes alkylation by controlling the $C_3$/iso-$C_5$ olefin ratio to reduce acid consumption. Another embodiment includes alkylation of $C_3$ and $C_5$ olefins in separate alkylation zones to maximize alkylate octane number. Even another embodiment includes propylene alkylation followed by $C_4$ and/or $C_5$ olefin alkylation, with the spent propylene acid used in the $C_4$ and/or $C_5$ olefin alkylation. Still another embodiment includes alkylation of $C_3$, $C_4$ and $C_5$ olefins in separate alkylation zones, with the spent propylene acid used in the $C_4$ alkylation, and the spent butylene acid used in the $C_5$ alkylation. Yet another embodiment includes alkylation by controlling the $C_3/C_4$ olefin ratio to maximize the octane number of the produced alkylate.

21 Claims, 17 Drawing Sheets

ALKYLATION BY CONTROLLING OLEFIN RATIOS

RELATED APPLICATION DATA

This application is a continuation-in-part of U.S. application Ser. No. 08/911,219 filed Aug. 15, 1997, now U.S. Pat. No. 5,841,014, which is a continuation of U.S. application Ser. No. 08/755,721 filed Nov. 25, 1996 now abandoned which is a continuation of U.S. application Ser. No. 08/315,926 filed Sep. 30, 1994 now abandoned.

BACKGROUND OF THE INVENTION

1. Field of the Invention

The present invention relates to alkylation. In another aspect, the present invention relates to alkylation of isoparaffins utilizing olefins. In even another aspect, the present invention relates to a process for the alkylation of isoparaffins utilizing olefins, which process results in reduced acid consumption. In still another aspect, the present invention relates to a process for the alkylation of isoparaffins utilizing olefins, which process results in an alkylate product having increased octane numbers. In yet another aspect, the present invention relates to alkylation of isoparaffins utilizing olefins by controlling the $C_3$ to $C_5$ olefin ratio. In even still another aspect, the present invention relates to alkylation of isoparaffins using $C_3$ and $C_5$ olefin separately. In even yet another aspect, the present invention relates to alkylation of isoparaffins utilizing propylene, followed by alkylation of isoparaffins utilizing $C_4$ and/or $C_5$ olefins. In still even another aspect, the present invention relates to isoparaffin alkylation utilizing separately, $C_3$, $C_4$ and $C_5$ olefins. In still yet another aspect, the present invention relates to alkylation of isoparaffins with $C_3$ to $C_4$ by controlling the $C_3$ to $C_4$ olefin ratio.

2. Description of the Related Art

As a result of the curtailment in the use of tetraethyl lead as an octane-improving additive for gasoline, not only has the production of unleaded gasoline increased but the octane number specification of all grades of gasoline have increased as well.

Additionally, recent reformulated gasoline specifications require a reduction in both the Reid Vapor Pressure ("RVP") and the olefin content. Alkylate is a low vapor pressure, high octane gasoline blending component containing essentially no olefins. Thus, alkylate helps refiners meet the new reduced RVP and reduced olefin content specifications. Additionally, alkylate burns cleanly, resulting in lower levels of undesired emissions from gasoline engines.

Isoparaffin-olefin alkylation processes are the key route to the production of these highly branched isoparaffin octane enhancers which are to be blended into gasolines, with alkylate typically comprising 10–15% of the gasoline pool.

Alkylation is a well known refinery process for converting light, gaseous olefins into high-octane gasoline components. Very simply, alkylation involves the addition of an alkyl group to an organic molecule. Thus, an isoparaffin can be reacted with an olefin to provide an isoparaffin of higher molecular weight. Generally, the alkylation of isoparaffins with olefins is accomplished by contacting the reactants with an acid acting catalyst such as hydrogen fluoride or sulfuric acid, settling the mixture to separate the catalyst from hydrocarbons, and further separating the hydrocarbons, usually by fractionation to recover alkylate product. The resulting alkylate product is typically a mixture of $C_5$ to $C_{16}$ isomers, with the exact composition depending upon the isoparaffin and olefin reactants used, as well as process conditions.

As practiced commercially, alkylation most commonly involves reacting an isoparaffin, comprising at least 75 weight percent isobutane and up to 25% isopentane, with $C_3$ to $C_5$ olefins in the presence of an acid catalyst, typically either hydrofluoric acid or sulfuric acid. The resulting alkylate product comprises predominately $C_7$ to $C_9$ isoparaffins, along with lesser amounts of lighter and heavier isoparaffins in the $C_6$ to $C_{16}$ range, and some isopentane.

Historically, $C_4$ olefins are preferred for use in alkylation, as they produce the highest octane alkylate with the lowest sulfuric acid catalyst consumption, on the order of about 0.5 pounds per gallon of alkylate product, as compared to propylene or $C_5$ olefins. In fact, an acid consumption of 0.5 pounds per gallon of alkylate represent about ⅓ of the alkylation operating costs.

Alkylation feeds in which the olefins consist of 100% propylene or 100% amylenes typically result in sulfuric acid catalyst consumption on the order of 1.0 to 2.0 pounds acid/gallon of alkylate produced, representing considerably more than ⅓ of the akylation operating cost. The higher sulfuric acid consumption, and lower octane numbers for the alkylate product, resulting from alkylation with propylenes and amylenes as compared to butylenes, makes these feed stocks economically unattractive, and therefore propylenes and amylenes are generally minimized in the alkyation feed.

However, many refiners have mixed olefins containing large amounts of propylene and/or amylenes which must be alkylated. Additionally, due to reformulated gasoline, Reid Vapor Pressure ("RVP"), D-86 distillation temperatures, and other requirements, increasing amounts of propylenes and amylenes are being alkylated and added to the gasoline pool.

Thus, while $C_4$ olefins are preferred for use in alkylation because of their low acid consumption, and resulting high-octane alkylate, alkylation with propylene may be necessary to meet product specifications. Other reasons for alkylating with propylene and/or amylenes include their ready availability, and unavailability of sufficient amounts of $C_4$ olefins for the amount of alkylate desired.

U.S. Pat. No. 2,242,845, issued Aug. 14, 1939 to Blount, discloses a process for alkylation of isobutane with a mixture of propylene and butylenes in the presence of sulfuric acid. For product yield, Blount discloses that the optimum alkylation temperature for alkylation of isobutane with butylene is about 30° F. to about 60° F., and for alkylation of isobutane with propylene is about 70° F. to about 100° F.

U.S. Pat. No. 2,351,464, issued Jun. 13, 1944 to Voorhies Jr. et al., discloses that it is well known to react olefins having from 2 to 5 carbons atoms with saturated hydrocarbons containing a tertiary carbon atom. The '464 patent further discloses that while alkylation with olefins having 3 or more carbon atoms has been entirely satisfactory, alkylation with ethylene has not been satisfactory due to excessive acid consumption. The '464 patent proposes that an acid employed for alkylation of olefins comprising ethylene, be separated and subsequently employed in the alkylation of olefins free of ethylene, without incurring any substantial acid consumption and with acid regeneration.

U.S. Pat. No. 2,491,618, issued Dec. 20, 1949 to Luetzelschwab discloses a catalytic contacting apparatus in which isoparaffinic and olefinic hydrocarbons may be introduced into the apparatus separately or admixed.

U.S. Pat. No. 3,045,055, issued Jul. 17, 1960 to Van Pool et al. generally disclose a process for the alkylation of a isoparaffin and the reforming of a hydrocarbon wherein each operation is arranged to benefit the other. Specifically, the process as disclosed by Van Pool et al. generally includes alkylation of an isoparaffin and an olefin in the presence of a hydrogen fluoride catalyst to obtain an alkylate effluent comprising an alkylate product, organic fluorides and normal isoparaffin. Van Pool et al. disclose that the charge materials introduced into the alkylation zone may include propylene, butylenes, amylenes, isobutane, isopentane, propyl fluorides, butyl fluorides, and amyl fluorides. Van Pool et al. further disclose that the preferred alkylation charge is an olefin-isoparaffin mixture, preferably a butylenes-isobutane mixture.

U.S. Pat. No. 3,211,803, issued Oct. 12, 1965 to Chapman discloses an alkylation process for the elimination of heavy alkylate utilizing both alkylation and reforming, with propylene and/or butylenes disclosed as the preferred olefins.

U.S. Pat. No. 3,502,569, issued Mar. 24, 1970 to Hervert discloses a process for the production of high octane motor fuel by alkylation and reforming. Hervert discloses that alkylation may be carried out by the catalytic alkylation of isobutane and/or isopentane with propylene, butylenes and amylenes. Specifically Hervert discloses alkylating isobutane with $C_4$ mono-olefin in the presence of an acid catalyst to produce an alkylate product containing dimethylhexanes. This alkylate is then separated into various fractions based on octane content. The lower-octane fraction is then reformed by admixture with hydrogen and a reforming catalyst. Finally, a portion of the reformate is commingled with the high-octane alkylate fraction to produce a suitable motor fuel alkylate. However, Hervert does not disclose or teach the problem of increased acid consumption by propylene, nor disclose or suggest a solution for such increased acid consumption.

U.S. Pat. No. 3,683,041, issued Aug. 8, 1972 to Goldsby, discloses alkylation encountering acidity run-aways. The '041 patent discloses that if run-away acid, the overall acid-hydrocarbon emulsion or reaction mixture produced during a run-away, or the alkylate produced and which contains sulfur, is charged to a normally operating alkylation reaction, that the acid can be restored to alkylation strength by alkylation of the alkyl sulfates, and the hydrocarbon portion of the reaction mixture can be freed of sulfur by extraction and alkylation of the alkyl sulfates.

U.S. Pat. No. 3,778,489, issued Dec. 11, 1973, to Parker et al., discloses an alkylation process which utilizes separate feed streams. Specifically, the '489 patent discloses that olefins which form tertiary carbonium ions under acidic conditions react unfavorably with terminal olefins not able to form tertiary carbonium ions under acidic conditions. According to the '489 patent, high octane alkylate is prepared by contacting a paraffin and a strong alkylation catalyst, in an alkylation zone, with a first olefin-containing stream substantially free of isobutylene and 2-methyl-butene-1 and a second olefin-containing stream comprising isobutylene, 2-methyl-butene-1 or mixtures thereof.

U.S. Pat. No. 3,998,903, issued Dec. 21, 1976 to Sobel, discloses an alkylation process utilizing an olefinic reactant containing 1-butene, 2-butene and isobutylene by fractionating the olefinic reactant into a 2-butene fraction and a separate 1-butene and isobutylene fraction. The 2-butene is charged to an HF alkylation reaction zone with isobutane. The mixture is heated by the heat of reaction, and the fraction comprising 1-butene and isobutylene is then added to the unitary reaction zone.

There is a need in the art for an improved alkylation process.

There is another need in the art for an improved alkylation process in which the acid catalyst consumption can be controlled and/or minimized.

There is even another need in the art for an improved alkylation process in which the octane number of the alkylate product can be controlled and/or maximized.

There is still another need in the art for an improved alkylation process for alkylating propylene or high propylene containing feeds, which is easier to operate than the known processes.

There is yet another need in the art for an alkylation process for alkylating amylene or high amylene containing feeds, which is easier to operate than the known processes.

There is even still another need in the art for an alkylation process for alkylating feeds having mixtures of propylene and amylenes.

There is even yet another need in the art for an alkylation process for alkylating feeds having mixtures of propylene and butylenes.

Other needs of the art will become evident to those of skill in the alkylation art upon reading this specification.

SUMMARY OF THE INVENTION

It is an object of the present invention to provide for an improved alkylation process.

It is another object of the present invention to provide for an improved alkylation process, in which the acid catalyst consumption can be controlled and/or minimized.

It is even another object of the present invention to provide for an improved alkylation process, in which the octane number of the resulting alkylate product can be controlled and/or maximized.

It is still another object of the present invention to provide for an improved alkylation process for alkylating propylene or high propylene containing feeds, which is easier to operate than the known processes.

It is yet another object of the present invention to provide for an alkylation process for alkylating amylene or high amylene containing feeds, which is easier to operate than the known processes.

It is even still another object of the present invention to provide for an alkylation process for alkylating feeds having mixtures of propylene and amylenes.

It is even yet another object of the present invention to provide for an alkylation process for alkylating feeds having mixtures of propylene and butylenes.

These and other objects of the present invention will become evident to those of skill in the alkylation art upon reading this specification.

According to one embodiment of the present invention there is provided a process for alkylating which includes contacting an olefin mixture comprising $C_3$ and $C_5$ olefins with an isoparaffin in the presence of an acid catalyst, to produce a first alkylate product. In this first alkylation zone, the mole ratio of $C_3$ olefins to $C_5$ olefins is in the range of about 30:70 to about 95:5. The benefits of this embodiment included reduced acid consumption within this preferred mole ratio range.

According to yet another embodiment of the present invention there is provided a process for alkylating which includes contacting an olefin mixture comprising $C_3$ olefins that is substantially free of $C_4$ and $C_5$ olefins, with an isoparaffin in the presence of an acid catalyst, to produce a first alkylate product and spent acid catalyst. This spent acid catalyst is then recovered to be used in a second alkylation zone, in which an olefin mixture comprising $C_4$ or $C_5$ olefins that are substantially free of $C_3$ olefins, are contacted with an isoparaffin, in the presence of the recovered acid catalyst to produce a second alkylate product and second spent acid. Further embodiments of this embodiment would include a third alkylation zone in which an olefin mixture comprising $C_4$ or $C_5$ olefins that are substantially free of $C_3$ olefins, are contacted with an isoparaffin, in the presence of the spent acid catalyst from the second alkylation to produce a third alkylate product and third spent acid product. Preferably, in a three alkylation process, $C_4$ olefins are utilized in the second alkylation and $C_5$ olefins are utilized in the third alkylation. Benefits of alkyating isoparaffins with $C_3$ olefins separately from $C_5$ olefins include an increase in the alkylate product octane number, as opposed to the octane number of alkylate product obtained from alkylating isoparaffins with a mixture of $C_3$ and $C_5$ olefins. Alkylate product quality is also enhanced by alkylating with propylene in an earlier, higher acidity alkyation reaction, and by alkylating with amylene in a later, lower acidity alkylation reaction. Additionally, a separate alkylation reaction for each olefin would allow for greater control over the final alkylate product, by selecting alkylation conditions for each alkylation reaction to achieve the desired product.

According to yet another embodiment of the present invention, there is provided a process for alkylating which includes contacting an olefin mixture comprising $C_3$ olefins that are substantially free of $C_5$ olefins, with an isoparaffin in the presence of an acid catalyst, to produce a first alkylate product. The method further includes contacting an olefin mixture comprising $C_5$ olefins that are substantially free of $C_3$ olefins, with an isoparaffin, in the presence of the spent acid catalyst from the first alkylation produce a second alkylate product. A variation of this embodiment would allow for the presence of other olefins in the $C_3$ or $C_5$ olefin stages, to the extent that the other olefins did not unduely effect the desired alkylate product.

According to even still another embodiment of the present invention there is provided a process for alkylating which includes contacting an olefin mixture including $C_3$ and $C_4$ olefins, with an isoparaffin in the presence of an acid catalyst, to produce alkylate product. By conducting the alkyation using from about 55 to about 99.5 weight percent $C_3$ olefin in the olefin mixture, based on the total weight of $C_3$ and $C_4$ olefins in the mixture, the alkylate product with have an octane number greater than the expected weighted average octane number.

DETAILED DESCRIPTION OF THE INVENTION

Figure 1:
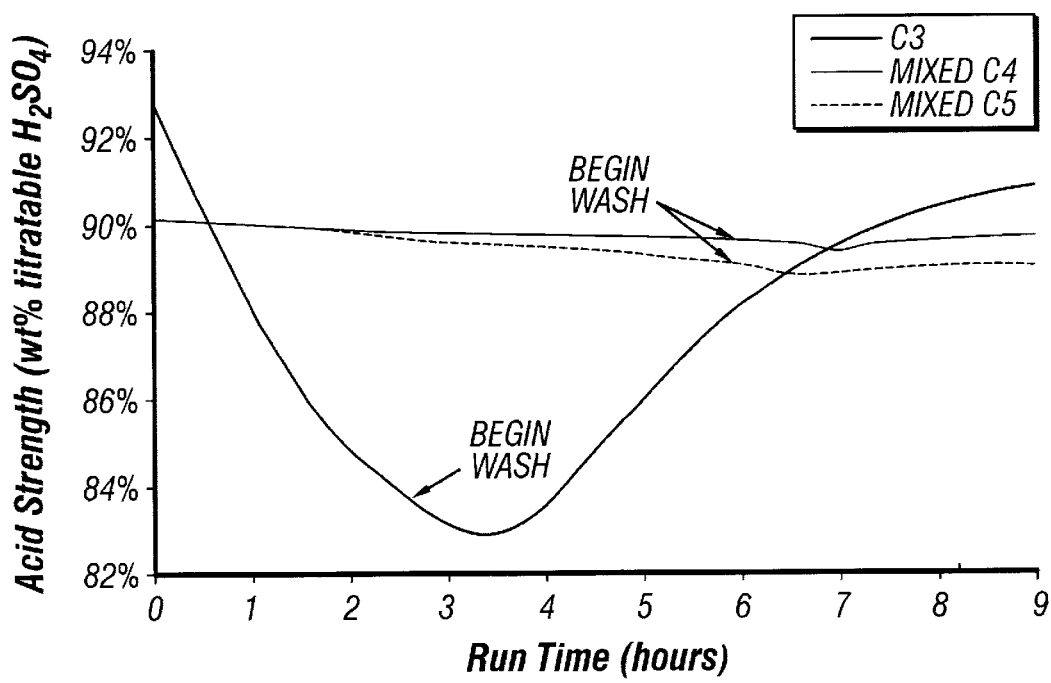
FIG. 1 is a graph of acid strength versus run time showing the effect of an isobutane wash for various olefin feeds.

The inventors have discovered various embodiments of their alkylation invention utilizing propylene, butylenes and/or amylenes, which show an improvement over the prior art limitations of high acid consumption and low octane alkylate.

"Acid consumption" as used herein relates to the dilution of the acid catalyst by acid soluble oils formed by undesirable side reactions. Additionally, formation of stable intermediates, such as sulfate esters when utilizing sulfuric acid catalyst, also dilute the catalyst causing an apparent acid consumption increase. "Acid strength" as used herein refers to the concentration of the acid catalyst, which for sulfuric acid is expressed in weight percent $H_2SO_4$ as determined by titration with standardized sodium hydroxide.

Among other things, the inventors have discovered that in alkylation processes, the type of olefins utilized with propylene and/or amylenes, the ratio of propylene to butylene, the ratio of propylene to amylene, and the stage of introduction of the propylene and/or amylenes into the reaction zone, are important parameters which influence acid consumption and the octane number of the alkylate. These and other discoveries will become readily apparent to those of skill in the art upon reading this specification.

Alkylation processes in general are well known to those of skill in the art. For example, see "Catalytic Alkylation", Petro/Chem Engineer, December 1961 and January 1962, "Alkylation will be key process in reformulated gasoline era", Oil & Gas Journal, Nov. 12, 1990, pp. 79–92, "$H_2SO_4$, HF processes compared, and new technologies revealed", Oil & Gas Journal, Nov. 26, 1990, pp. 70–77, and "Which alkylation—HF or $H_2SO_4$?", Hydrocarbon Processing, September 1985, all herein incorporated by reference. Additionally, alkylation is generally disclosed in U.S. Pat. Nos. 4,018,846; 4,225,740; 4,276,731; 4,371,731; 4,383,977; 4,404,418; 4,467,131; 4,513,165; 4,777,323; and 5,157,196; all herein also incorporated by reference.

In the practice of the alkylation process of the present invention, the precise process steps and process conditions will vary somewhat depending upon the catalyst system utilized, the alkylate product desired, available equipment, process economics and other factors. It is anticipated that any suitable catalyst may be utilized, including liquid, solid or any other type of catalyst.

In the practice of the present invention, a suitable olefin is alkylated with a suitable isoparaffin, in the presence of a suitable catalyst to product the desired alkylate product. The reacting hydrocarbons may generally include olefins having two or more carbons atoms, as well as isoparaffins having four or more carbon atoms. Preferably, the reacting hydrocarbons include olefins having three to five carbon atoms, and isoparaffins having from three to four carbon atoms.

Embodiment 1
Acid Consumption Reduction By Alkylation of $C_3$/$C_5$ Olefins at Certain Ratios As explained in the Background, alkylation of an isoparaffin with 100% propylene or 100% amylenes results in high sulfuric acid catalyst consumption on the order of 1.0 to 2.0 pounds acid per pound of alkylate produced, but alkylation utilizing propylene or amylenes may be necessary to meet certain product specifications.

The inventors have discovered that acid consumption actually decreases substantially for certain mixtures of $C_3$ and $C_5$ olefins, as opposed to alkylation with either 100% propylene or 100% amylenes, or as opposed to the predicted weighted average acid consumption for a mixture.

In the practice of this embodiment of the present invention, the ratio of $C_3$ to $C_5$ olefins in the olefin feed utilized will be suitable to reduce the acid consumption to a desired level and produce alkylate product. Generally for this embodiment, the mole ratio of $C_3$ to $C_5$ olefins in the olefin feed utilized will be suitable to provide acid consumption below the predicted weighted average acid consumption, and such a ratio will generally be in the range of about 30:70 to about 95:5. Preferably, the mole ratio of $C_3$ to $C_5$ olefins utilized will be in the range of about 35:65 to about 90:10, more preferably in the range of about 40:60 to about 90:10, and most preferably in the range of about 45:55 to about 85:15. The mole ratio of $C_3$ to iso-$C_5$ olefins will generally be in the range of about 45:55 and about 95:5. Preferably, the mole ratio of $C_3$ to iso-$C_5$ olefins will be in the range of about 65:35 and about 90:10, more preferably in the range of about 70:30 and about 90:10 and most preferably in the range of about 75:25 and about 90:10. It is noted that there will be a tradeoff between acid consumption savings, and loss in octane number.

Additionally, in the practice of this embodiment of the present invention, the $C_5$ olefins utilized will generally comprise branched and linear isomers in the range of about 10:90 to about 90:10 mole ratio of branched to linear isomers. Preferably, the $C_5$ olefins utilized will generally comprise branched and linear isomers in the range of about 25:75 to about 75:25 mole ratio of branched to linear isomers, and most preferably in the range of about 40:60 to about 60:40 mole ratio of branched to linear isomers.

Generally, other olefins may be present as long as their presence is not unduly detrimental to acid consumption, and as long as the proper ratio of $C_3$ to $C_5$ olefins is maintained.

In the practice of this embodiment of the present invention, although any suitable isoparaffin that can be alkylated to provide the desired alkylate product may be utilized, it is preferred to utilize isobutane as the isoparaffin. Although not preferred, isopentane can be substituted for isobutane, to the extent that a suitable product can be obtained, or reasonable process conditions may be utilized. If isopentane is substituted for isobutane, the isoparaffin will generally comprise no more than about 25 weight percent isopentane.

This embodiment of alkylating with certain ratios of $C_3$ and $C_5$ olefins, may be carried out in any suitable reactor or reactors, including commercially known multistage reactors. It is to be understood that the acid may be cascaded from one reaction stage to the next. Alternatively, the various hydrocarbon feeds may be switched between stages, with the spent acid remaining in each stage.

It is generally desirable that the $C_3/C_5$ olefin mixture be reacted at higher acid concentrations. Thus, when utilizing a multi-stage alkylation process in which the acid catalyst is being cascaded from one stage to the next, the $C_3/C_5$ olefin mixture is generally alkylated in one of the earlier, higher acid concentration stages.

For example, in a two stage reactor system, the $C_3$ and $C_5$ olefin mixtures may be alkylated with isobutane in the presence an acid catalyst in the first stage reactor. $C_4$ and/or $C_5$ olefins substantially free of $C_3$ olefins are then alkylated in the second stage using acid catalyst from the first alkylation stage. Alternatively, instead of cascading the acid catalyst, the $C_3$ and $C_5$ olefin feeds may be switched.

As another example, $C_4$ and/or $C_5$ olefins substantially free of $C_3$ olefins are alkylated with isobutane in the presence an acid catalyst in the first reactor. The $C_3$ and $C_5$ olefins may then be alkylated in the second stage reactor using acid catalyst from the first alkylation stage. Again, instead of cascading the acid catalyst, the $C_3$ and $C_4/C_5$ olefin feeds may be switched.

Utilizing spent acid catalyst in subsequent alkylation reactions has the effect of "washing" the acid, which refers to the removal or further reaction of alkyl sulfate ester intermediates present in the acid which also dilute the acid to give an apparent acid consumption.

Embodiment 2
Increasing Octane Number By Alkylating $C_3$ and $C_5$ Olefins in Separate Alkylation Reactors In the last embodiment, alkylating isoparaffins with a mixture of $C_3$ and $C_5$ olefins at a certain ratio yielded an alkylate product at an acid consumption rate below the expected weighted average acid consumption rate. Unfortunately, there is a decrease in the octane number of the alkylate product. In the processing of such $C_3$ to $C_5$ olefins, it may be desirable to produce an alkylate having an increased octane number.

Figure 26:
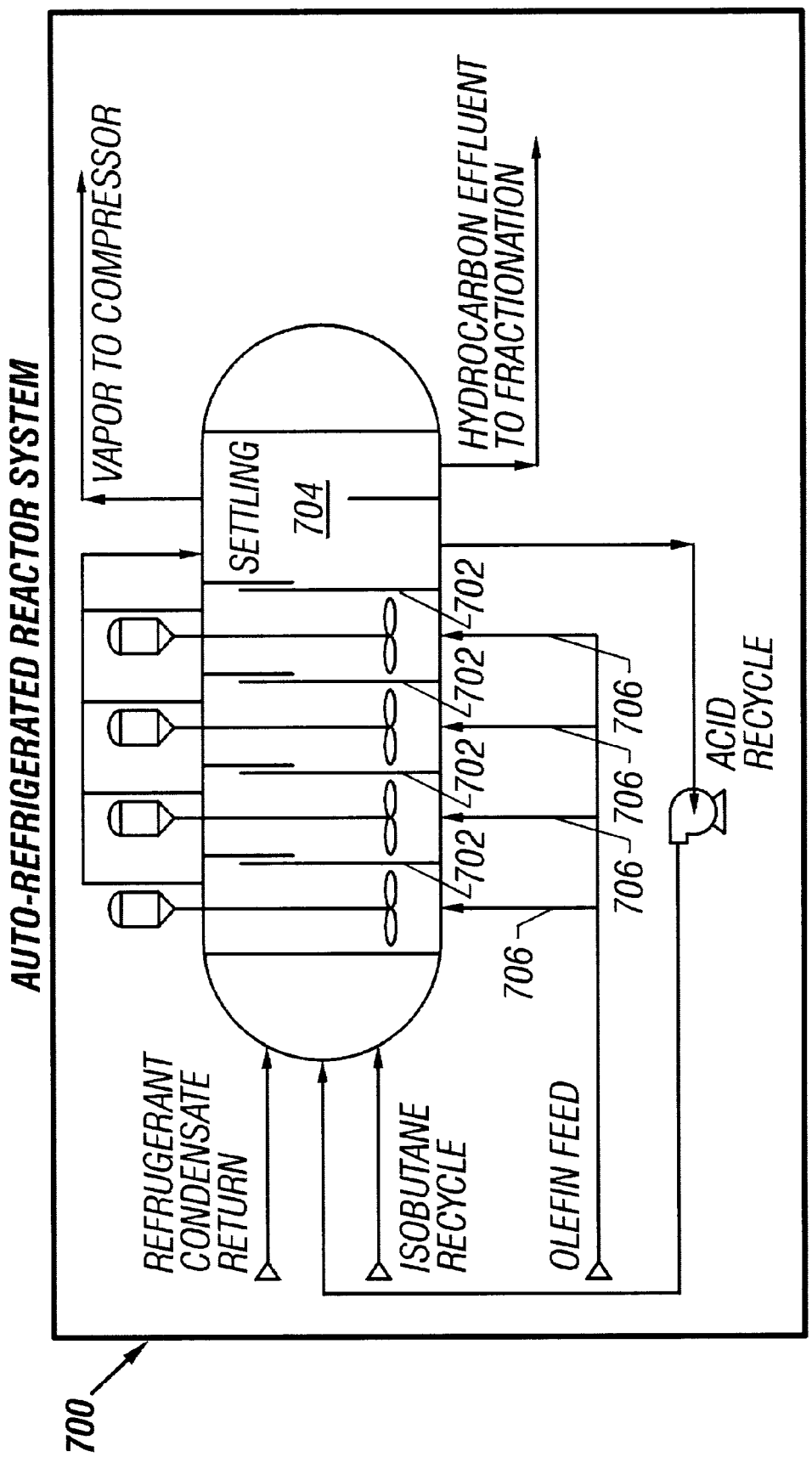
FIG. 26 an illustration of a single reactor system 700 having several reaction zones or compartments 702A–D with olefin feeds 706A–D within one vessel.

As opposed to the last embodiment in which the $C_3$ and $C_5$ olefins were reacted together in the same alkylation reaction, the method of this embodiment alkalytes $C_3$ and $C_5$ olefins in separate alkylation reactors. Alternately, as illustrated in FIG. 26, the method of this embodiment may be practiced in a single reactor system having several zones or compartments within one vessel, the compartments or zones allowing the separate alkylation of the separate olefin feeds.

In the method of this embodiment, an olefin mixture comprising $C_3$ olefins substantially free of $C_5$ olefins is contacted in a first reaction zone with an isoparaffin in the presence of a suitable catalyst to form an alkylate product. In a second reaction zone, an olefin mixture comprising $C_5$ olefins substantially free of $C_3$ olefins is contacted with an isoparaffin in the presence of a suitable catalyst to form a second alkylate product. The catalyst utilized in the second reaction zone is the recovered spent catalyst from the first reaction zone.

Alternatively, the hydrocarbon feeds to each of the reaction zones may be switched, with the spent catalysts remaining in each zone. For example, see FIG. 24B a schematic showing that the olefin feeds can be switched between reaction zones 1 and 2.

Figure 24A:
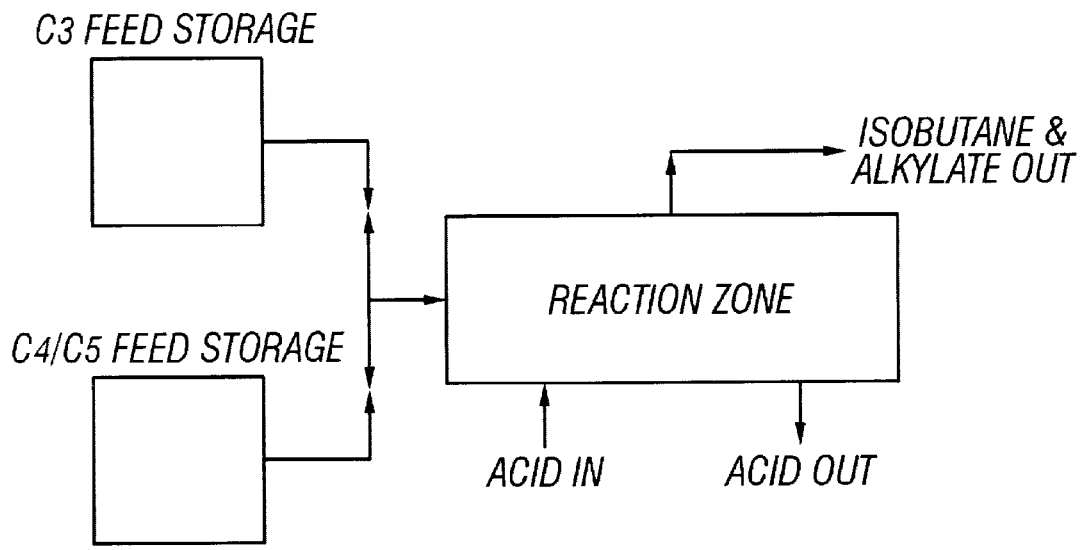
FIG. 24A and FIG. 24B are schematics comparing respectively, a single reaction zone alkylation in which the olefin feeds are mixed prior to alkylation, to a two reaction zone alkyation in which different olefins are feed to each alkylation zone.
Figure 24B:
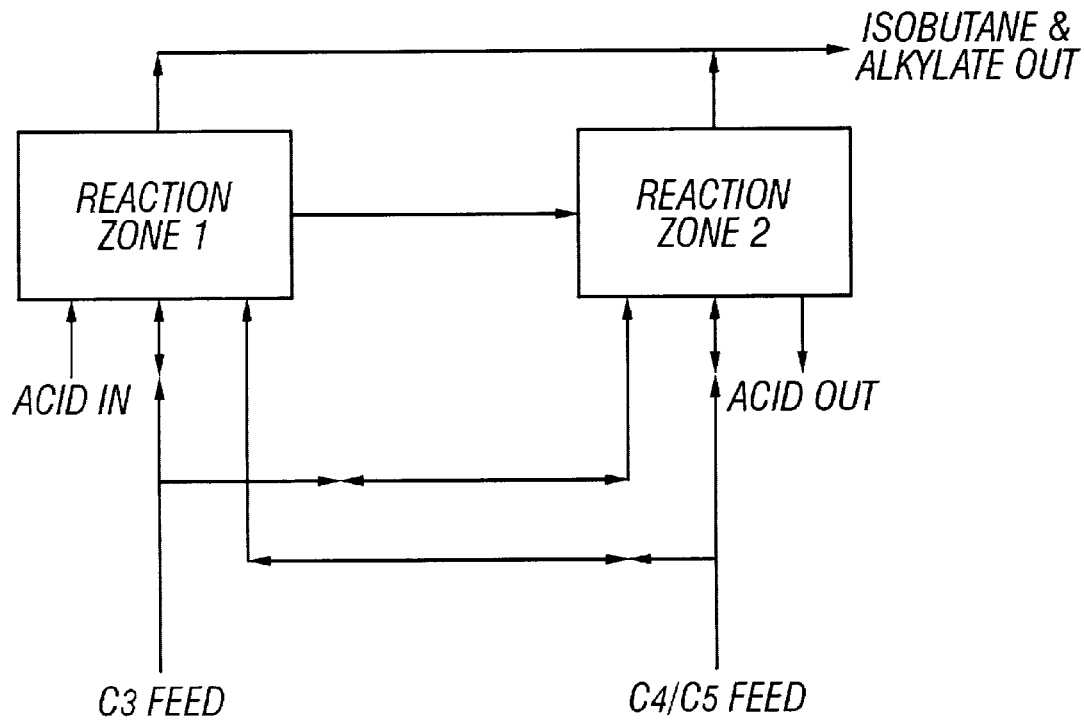

It is also possible to carry out the two alkyation reactions consecutively in one reactor as shown in FIG. 24A. For example, isobutane and propylene are provided to the reaction zone. Subsequently, the propylene feed may be stopped and amylenes, optionally with butylenes, can be provided to the reaction zone to alkylate isobutane.

It is still also possible to carry out the two alkylation reactions in a single zoned or compartmentalized reactor. For example, in the auto-refrigeration reactor system shown in FIG. 26 the reactor system shown generally as 700 includes reaction zones or compartments 702A, 702B, 702C and 702D, and settler area 704. One or more olefin feeds 706A and B may be introduced into compartments 702A–D. It is contemplated that one olefin feed 706A, B, C, or D could be a $C_3$ olefin mixture that is substantially free of $C_5$ olefins and at least one additional olefin feed 706A, B, C, or D could be a $C_5$ olefin mixture that is substantially free of $C_3$ olefins.

The $C_3$ olefin mixture that is substantially free of $C_5$ olefins, will comprise at least 50 weight percent $C_3$ olefins, having no more than 50 weight percent $C_5$ olefins. Preferably, the $C_3$ olefin mixture will comprise at least about 75 weight percent $C_3$ olefins, having no more than about 25 weight percent $C_5$ olefins, and more preferably at least about 90 weight percent $C_3$ olefins, having no more than about 10 weight percent $C_5$ olefins, and most preferably at least about 95 weight percent $C_3$ olefins, having no more than about 5 weight percent $C_5$ olefins.

The $C_5$ olefin mixture that is substantially free of $C_3$ olefins, will comprise at least 50 weight percent $C_5$ olefins, having no more than 50 weight percent $C_3$ olefins. Preferably, the $C_5$ olefin mixture will comprise at least about 75 weight percent $C_5$ olefins, having no more than about 25 weight percent $C_3$ olefins, and more preferably at least about 90 weight percent $C_5$ olefins, having no more than about 10 weight percent $C_3$ olefins, and most preferably at least about 95 weight percent $C_5$ olefins, having no more than about 5 weight percent $C_3$ olefins.

In the operation of this embodiment of the present invention, $C_4$ olefins may be present in both the first and second reaction zones. It is preferred however, that if $C_4$ olefins are alkylated with $C_3$ olefins, that $C_3$ olefins comprise at least 55 mole percent of the feed, based on the total moles of $C_3$ and $C_4$ olefin in the feed. Again, the second alkylation reaction will serve to wash the spent acid from the first alkylation reaction.

The inventors have also discovered that $C_3$ olefins alkylate isoparaffins more effectively at higher acidities, whereas, acidity is not as critical in the alkylation of isoparaffins with $C_5$ olefins. Therefore, it is preferred that in the practice of the present embodiment, that $C_3$ olefins be utilized in the higher acidity alkylation zone, and that $C_5$ olefins be utilized in the lower acidity alkyation zone. Thus, the propylene acid from the propylene alkylation will be washed in the subsequent alkylation. The term "alkylene acid" with specific alkylene named, refers to acid that has been used in the alkyation of that named alkylene.

Generally, for the propylene alkylation, acid catalyst consumption decreases, and octane number of the alkylate product increases, with decreasing olefin space velocity.

As used herein, "olefin space velocity" is defined as the volume of olefins charged to the reaction zone per hour divided by the average amount of acid in the reactor. Residence time of the hydrocarbons in the reactor is inversely proportional to the olefin space velocity, i.e., when the space velocity increases, the residence time of the hydrocarbons in the reactor decreases. A doubling of the space velocity nearly halves the residence time.

It is desirable to operate the propylene alkylation at a high acid concentration. For example, for propylene alkylation using sulfuric acid catalyst, the acid strength is generally in the range of about 85 to about 99.5 percent. Preferably, the acid strength is at least about 90 percent, and most preferably, the acid strength is at least about 92 percent.

By utilizing the spent propylene acid in the amylene alkylation zone, this subsequent $C_4$ and/or $C_5$ olefin alkylation stage serves to wash the propylene acid to restore some or substantially all of the acid strength after it has been diluted by the propylene alkylation stage.

Embodiment 3
Alkylation Utilizing a Propylene Alkylation Stage That is Followed By a $C_4$ and/or $C_5$ Olefin Alkylation Stage In the alkylation of isoparaffins with $C_3$ to $C_5$ olefins, this embodiment of the present invention provides a method of alkylation in which there is a propylene alkylation stage that is followed by a subsequent $C_4$ and/or $C_5$ olefin alkylation stage. This subsequent $C_4$ and/or $C_5$ olefin alkylation wash stage serves to restore some or substantially all of the acid strength after it has been diluted by the propylene alkylation stage.

For example, in a three stage process, the first stage alkylates isoparaffins with $C_3$ olefins, the second stage alkylates isoparaffins with $C_4$ olefins, and the third stage alkylates isoparaffins with $C_5$ olefins.

Alkylation reactants have a residence time in the subsequent $C_4$ and/or $C_5$ olefin alkylation stage for a period of time necessary to achieve the desired acid strength and produce the desired product. Generally this means that in the subsequent $C_4$ and/or $C_5$ olefin alkylation stage, the reactants have a residence time in the range of about 0.1 to about 100 minutes. Preferably, the subsequent $C_4$ and/or $C_5$ olefin alkylation stage is operated such that the reactants have a residence time in the range of about 1 to about 30 minutes, and most preferably in the range of about 5 to about 20 minutes.

In this embodiment, at least a portion of the acid catalyst from the propylene alkylation stage is provided to the subsequent $C_4$ and/or $C_5$ olefin alkylation stage. Alternatively, instead of routing the acid between the stages, the hydrocarbons feeds could be switched between the various stages.

In addition to propylene, the propylene alkylation stage may utilize some amounts of $C_4$ and/or $C_5$ olefins. However, preferably, the propylene alkylation stage will be substantially free of $C_4$ and/or $C_5$ olefins. In the propylene alkylation stage, the olefin utilized will generally comprise at least 50 volume percent propylene, preferably at least 75 volume percent propylene, and most preferably at least 90 volume percent propylene. The stage or stages that follow the propylene alkylation stage will be substantially free of propylene. Generally in the stage or stages following the propylene alkylation stage, the olefin utilized will comprise less than about 50 volume percent propylene, preferably less than about 25 volume percent propylene, and most preferably less than about 10 volume percent propylene.

Generally, for the propylene alkylation, acid catalyst consumption decreases, and octane number of the alkylate product increases, with decreasing olefin space velocity.

It is desirable to operate the propylene alkylation at a high acid concentration. For example, for propylene alkylation using sulfuric acid catalyst, the acid strength is generally in the range of about 85 to about 99.5 percent. Preferably, the acid strength is at least about 90 percent, and most preferably, the acid strength is at least about 92 percent.

An example of equipment suitable for use with this embodiment includes two alkylation reactors which are both connected to the same acid settler. For example, in one reactor, alkylation occurs by contacting $C_3$ olefins substantially free of $C_4$ olefins, with an isoparaffin in the presence of an acid catalyst, to produce a first alkylate product. In the other reactor, $C_4$ olefins substantially free of $C_3$ olefins, are contacted with an isoparaffin in the presence of an acid catalyst, to produce a second alkylate product. Reactor effluent, comprising an acid and alkylate phase, from the $C_3$ and $C_4$ reactors is recovered in the acid settler. Once the acid is settled from the reactor effluent and separated from the alkylate, one portion of the recovered acid catalyst is recycled back to the $C_3$ reactor, and another portion of the recovered acid catalyst is recycled back to the $C_4$ reactor.

Figure 27:
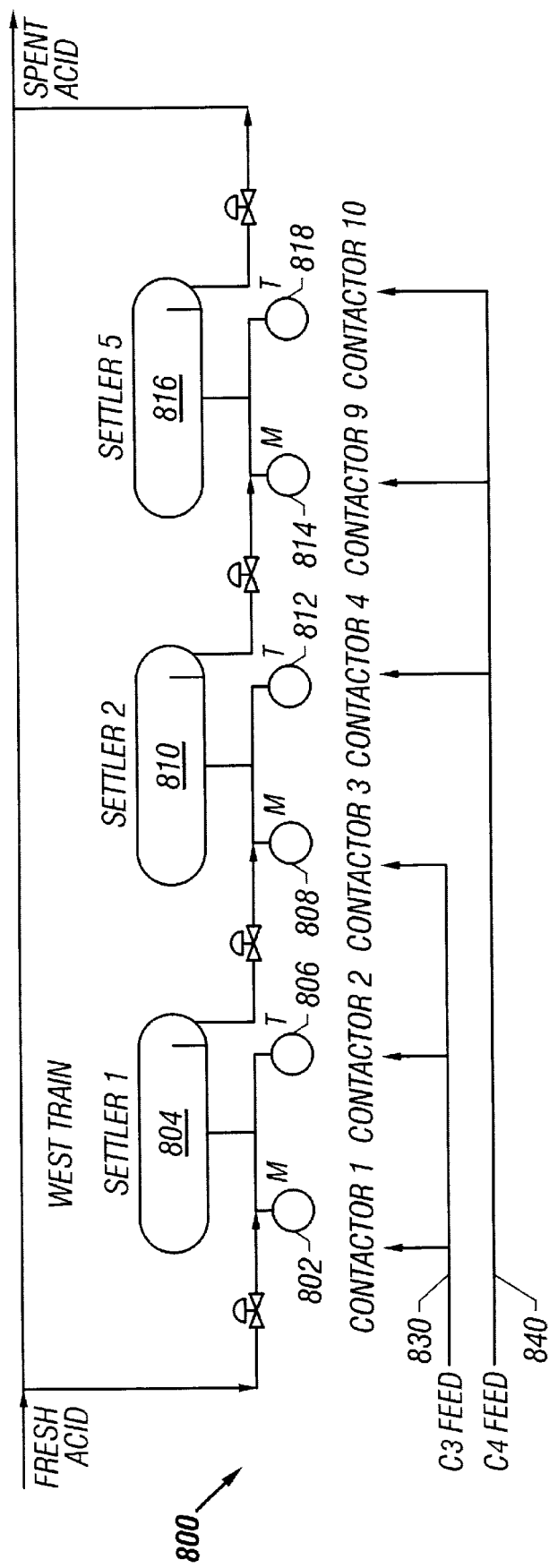
FIG. 27 is an illustration of reaction system 800 where reactors 802 and 806 share acid settler 804, reactors 808 and 812 share settler 810, and reactors 814 and 818 share settler 816.

Referring to FIG. 27, Equipment of this type may also be utilized in series. The system, shown generally as 800, includes multiple alkylation reactors connected to the same acid settler. As shown in FIG. 27, for example, reactors 802 and 806 share acid settler 804, reactors 808 and 812 share settler 810, and reactors 814 and 818 share settler 816. Reactors 802, 806 and 808 receive an $C_3$ olefin feed 830 substantially free of $C_4$ olefins while reactors 812, 814 and 818 receive an $C_4$ olefin feed 840 substantially free of $C_3$ olefins. As above, reactor effluent comprising an acid and alkylate phase is recovered from each acid settler and the acid catalyst is recycled as desired.

Embodiment 4
Alkylation Utilizing a Separate Alkylation Stage for Each of $C_3$, $C_4$ and $C_5$ Olefins This embodiment requires the complete separation of $C_3$ from $C_4$ from $C_5$ olefins, with each separated olefin to be alkylated in a separate reactor at optimum alkylation conditions. Alternately, each separated olefin may be alkylated in a separate zone or compartment of a single reactor at optimum alkylation conditions. In such a multistage alkylation system, the propylene stage is preferably followed by a $C_4$ or $C_5$ olefin stage to help increase the acid strength, and the $C_5$ olefin stage is preferably the last stage as $C_5$ olefin alkylation can tolerate lower acid strengths without suffering any undue effects on acid consumption or octane number of the produced alkylate product.

Each olefin alkylation stage will be "substantially free" of the other olefins. For example, the $C_3$ olefin alkylation stage will be substantially free of $C_4$ and $C_5$ olefins. Substantially free generally means that the olefin is at least 50 weight percent pure. Preferably, substantially free means that the olefin is at least 75 percent pure, more preferably at least 90 percent pure, and most preferably, at least 95 percent pure.

For example, a propylene alkylation stage for alkyating isoparaffins with propylene will generally utilize an olefin that comprises at least 50 weight percent propylene, and not more than 50 weight percent other olefins. Preferably, the olefin would comprise at least 75 weight percent propylene, and not more than 25 weight percent other olefins; more preferably, the olefin would comprise at least 90 weight percent propylene, and not more than 10 weight percent other olefins, and most preferably, the olefin would comprise at least 95 weight percent propylene, and not more than 5 weight percent other olefins.

The main advantage of alkylating each olefin in a dedicated reaction zone is that the process parameters in each zone can be varied to achieve the desired alkylation product.

Generally, in the operation of the $C_3$ olefin alkylation zone, the alkylation temperature is in the range of about 40° F. to about 100° F., the acid strength is generally in the range of about 99 to about 85, the ratio of acid to hydrocarbons is in the range of about 1:2 to about 3:1, the isoparaffin to olefin ratio is generally in the range of about 1 to about 50 and the residence time of the reactants in the alkylation zone is in the range of about 0.1 to about 100 minutes. Preferably, in the operation of the $C_3$ olefin alkylation zone, the alkylation temperature is in the range of about 45° F. to about 70° F., the acid strength is at least about 90, and the ratio of acid to hydrocarbons is in the range of about 2:5 to about 3:1, the isoparaffin to olefin ratio is generally in the range of about 2 to about 20, and the residence time of the reactants in the alkylation zone is in the range of about 1 to about 30 minutes. Most preferably, in the operation of the $C_3$ olefin alkylation zone, the alkylation temperature is in the range of about 55° F. to about 65° F., the acid strength is at least about 92, the ratio of acid to hydrocarbons is in the range of about 1:1 to about 2:1, the isoparaffin to olefin ratio is generally in the range of about 5 to about 14, and the residence time of the reactants in the alkylation zone is in the range of about 5 to about 20 minutes.

Generally, in the operation of the $C_4$ olefin alkylation zone, the alkylation temperature is in the range of about 30° F. to about 70° F., the acid strength is generally in the range of about 99 to about 85, the ratio of acid to hydrocarbons is in the range of about 1:2 to about 3:1, the isoparaffin to olefin ratio is generally in the range of about 1 to about 50, and the residence time of the reactants in the alkylation zone is in the range of about 0.1 to about 100 minutes. Preferably, in the operation of the $C_4$ olefin alkylation zone, the alkylation temperature is in the range of about 40° F. to about 60° F., the acid strength is at least about 88, and the ratio of acid to hydrocarbons is in the range of about 1.2 to about 3:1, the isoparaffin to olefin ratio is generally in the range of about 2 to about 20, and the residence time of the reactants in the alkylation zone is in the range of about 1 to about 30 minutes. Most preferably, in the operation of the $C_4$ olefin alkylation zone, the alkylation temperature is in the range of about 45° F. to about 55° F., the acid strength is at least about 90, the ratio of acid to hydrocarbons is in the range of about 1:1 to about 2:1, the isoparaffin to olefin ratio is generally in the range of about 5 to about 14, and the residence time of the reactants in the alkylation zone is in the range of about 5 to about 20 minutes.

Generally, in the operation of the $C_5$ olefin alkylation zone, the alkylation temperature is in the range of about 30° F. to about 70° F., the acid strength is generally in the range of about 99 to about 85, the ratio of acid to hydrocarbons is in the range of about 1:2 to about 3:1, the isoparaffin to olefin ratio is generally in the range of about 1 to about 50, and the residence time of the reactants in the alkylation zone is in the range of about 0.1 to about 100 minutes. Preferably, in the operation of the $C_5$ olefin alkylation zone, the alkylation temperature is in the range of about 40° F. to about 60° F., the acid strength is at least about 88, and the ratio of acid to hydrocarbons is in the range of about 1.2 to about 3:1, the isoparaffin to olefin ratio is generally in the range of about 2 to about 20, and the residence time of the reactants in the alkylation zone is in the range of about 1 to about 30 minutes. Most preferably, in the operation of the $C_5$ olefin alkylation zone, the alkylation temperature is in the range of about 45° F. to about 55° F., the acid strength is at least about 90, the ratio of acid to hydrocarbons is in the range of about 2:5 to about 2:1, the isoparaffin to olefin ratio is generally in the range of about 5 to about 14, and the residence time of the reactants in the alkylation zone is in the range of about 5 to about 20 minutes.

For example, one variation of this embodiment is the "$C_3$, $C_4$ and $C_5$" order. In a first alkylation zone, $C_3$ olefins substantially free of $C_4$ and $C_5$ olefins, are contacted with an isoparaffin in the presence of an acid catalyst, to produce a first alkylate product. While most of the acid catalyst is recycled back to the alkyation zone, at least a portion of the acid catalyst is then recovered to be reused in a subsequent reaction stage in which $C_4$ olefins substantially free of $C_3$ and $C_5$ olefins, are contacted with an isoparaffin to produce a second alkylate product. Again, while most of the acid is recycled, at least a portion of the acid catalyst from this second stage is recovered to be reused in a subsequent stage in which $C_5$ olefins substantially free of $C_3$ and $C_4$ olefins, are contacted with an isoparaffin to produce a third alkylate product. Such a "$C_3$, $C_4$ and $C_5$" order allows propylene to be reacted with the highest acid strength to minimize acid catalyst consumption, and allows butylenes to be reacted at an intermediate acid strength and amylenes to be reacted at the lowest acid strength to maximize alkylate octane number. Alternatively, it is to be understood that instead of cascading the spent acid catalyst between the various stages, the hydrocarbon feeds can be switched between the various stages.

A two stage example would include a first stage for alkylating $C_3$ olefins substantially free of $C_4$ and $C_5$ olefins. The spent propylene acid from this $C_3$ olefin alkylation stage is routed to be washed in a second stage in which $C_4$ and/or $C_5$ olefins substantially free of $C_3$ olefins are used to alkylate isoparaffins. Again, it is to be understood that instead of cascading the spent acid catalyst between the various stages, the hydrocarbon feeds can be switched between the various stages.

Embodiment 5

Increasing Octane Number For Propylene/Butylene Blends

Alkylation of isobutane with butylene will produce an alkylate product having a motor octane number of about 94.2, and alkylation of isobutane with propylene will produce an alkylate product having a motor octane number of about 90.0. The general teaching in the art is that propylene should be minimized in alkylation, as alkylation with a mixture would produce an alkylate product having a motor octane number that is a weighted average of 94.2 and 90.0, depending upon the ratio of the mixture. Unfortunately, in many instances, the feed to the alkylation unit will contain both butylene and some amount of propylene.

The inventors have discovered that the octane number can be increased above the weighted average by alkylating with a propylene/butylene having a volume ratio of propylene:butylene in the range of about 99:1 to about 55:45. The inventors have also discovered, that outside of this range, the octane number will actually be below the weighted average. This effect can be seen by referring to FIG. 11, a graph of octane number versus weight percent $C_4$ olefin in a $C_3/C_4$ olefin feed showing both actual data, and predicted results, which figure is further discussed in Example 10 below.

Thus, the common teaching of minimizing the amount of propylene in a propylene/butylene alkylation mixture actually produces alkylate product with an octane number below the weighted average.

To achieve greater than theoretical octane numbers when processing a propylene/butylene alkylation feed having from 0 to 45 weight percent propylene, the method of the present embodiment provides that a sufficient amount of propylene be present or be included such that propylene comprises 55 to 99 weight percent propylene/butylene feed.

Alkylation with a propylene/butylene alkylation mixture is carried out utilizing known alkylation process conditions.

General Conditions for all Embodiments

It is to be understood that the above embodiments which utilize subsequent alkyation reactions for washing spent acid from earlier alkyation reactions, can be utilized in normally running alkylation reactions, as well as those reactions in a run away condition. In most alkyation reactions, the acid strength of the spent acid is monitored with fresh acid being added to maintain acid strength. Normal alkylation conditions will be present when the acid strength of the alkylation reaction can generally be maintained by the addition of fresh acid.

Unless specified above, the above embodiments may be conducted at the following conditions.

The alkylation process of the present invention is generally operated with ratios of isoparaffin to olefin in the feed streams to the reactor of greater than 1 to minimize undesired polymerization reactions. The isoparaffin to olefin ratio is generally in the range of about 2:1 to about 50:1, and preferably in the range of about 4:1 to about 20:1. Most preferably for hydrogen fluoride catalyzed alkylation, the isoparaffin to olefin ratio is in the range of about 10:1 to about 15:1. Most preferably for sulfuric acid catalyzed alkylation, the isoparaffin to olefin ratio is in the range of about 5:1 to about 12:1.

For the present invention the alkylation is generally carried out by contacting the catalyst and the reacting hydrocarbons in a reactor under closely controlled conditions. Alkylation reactions are very exothermic and require cooling to remove the heat of reaction from the reactor.

Reactor systems useful in the practice of the present invention include time-tank or pipe reactors, the Stratco® Contactor reactor, cascade reactors, gravity reactors, solid catalyst reactors, and the like, and other types of alkylation reactors known to those of skill in the alkylation art.

The catalyst and the reacting hydrocarbons are generally contacted together in the reactor utilizing a sufficient level of agitation to provide intimate contact between the two liquid phases. High levels of agitation are generally more important for sulfuric acid alkylation than for HF alkylation. The agitation is generally provided utilizing baffling, positioning of the impeller and by recycle streams.

Additionally, with some reactor systems, the hydrocarbons may be contacted with a liquid catalyst in the form of a fine dispersion in the liquid catalyst. The hydrocarbon droplet size utilized will be in the range of about 10 to about 1000 microns, preferably about 10 to about 100 microns to give good contact with the catalyst. The fine dispersion of hydrocarbons may be obtained by any suitable method, including introducing the hydrocarbons into the reactor at high velocity through nozzles, by utilizing a high shear mechanical device such as a centrifugal pump, by utilizing a static mixer, or by any other suitable method.

The alkylation catalyst utilized in the present alkylation invention may be any catalyst that will catalytically effect the reaction of the isoparaffins and olefins. Suitable catalysts include strong acid catalysts such as hydrofluoric acid, sulfuric acid, phosphoric acid, mixtures of sulfuric and phosphoric acids, metal halides such as aluminum chloride or aluminum bromide, certain complexes of aluminum chloride and sulfuric acid, and the like. It is also within the scope of this invention to effect the alkylation by contacting the alkylation reactants with a suitable solid alkylation catalyst. Solid catalysts such as macroreticular acidic ion exchange resins in the presence of $BF_3$ and zeolite catalysts can also be utilized. Also, solid catalysts such as acid washed silica treated with antimony pentafluoride, and preferably activated at low temperature with an alkane or isoparaffin may be utilized. Preferably, the alkylation catalyst utilized in the present invention is hydrofluoric acid or sulfuric acid.

Acid strength of the catalyst utilized in the present invention is generally maintained high enough to avoid dilution of the acid catalyst but low enough to avoid excessive side reactions. For example, the range of useful strengths of sulfuric acid is generally in the range of about 86 to about 99 weight percent.

The volume ratio of catalyst to total hydrocarbons is generally in the range of about 10:1 to about 1:10, and preferably in the range of about 10:1 to about 1:2.

The alkylation temperature and pressure utilized in the present invention is generally selected to yield the desired alkylation products without undue detrimental effects upon the catalyst or alkylation reactants.

Generally, the alkylation temperature utilized in the present invention is in the range of about −60° F. to about 1000° F. Preferably, the alkylation temperature utilized in the present invention is in the range of about −40° F. to about 200° F., more preferably in the range of about 35° F. to about 200° F., and most preferably in the range of about 35° F. to about 125° F. It is observed that at lower temperatures the rate of reaction is generally slower, and at higher temperatures, some cracking, polymerization and carbon formation occurs. The alkylation temperature utilized will generally also be influenced by economy of equipment and operating costs.

Additionally, it is also noted that the most preferred alkylation temperatures will also vary depending upon the type of catalyst utilized. The upper limit on the alkylation temperature is generally selected to avoid undue temperature degradation of the catalyst and to keep the catalyst in the desired state. For example, with sulfuric acid catalysts, the alkylation temperature is most preferably in the range of about 40° F. to about 60° F. and generally requires some type of refrigeration, while the most preferable alkylation temperature when utilizing hydrogen fluoride catalysts is in the range of about 85° F. to about 115° F., which can generally be maintained utilizing cooling water. For solid catalysts such as acid washed silica treated with antimony pentafluoride, the preferred alkylation temperature is in the range of about −58° F. to about 212° F.

The alkylation pressure utilized in the present invention is generally selected to maintain at least a portion of, and preferably a majority of, the hydrocarbon reactants in a liquid phase. Generally, the reaction pressure is in the range of about atmospheric to about 5000 psi or more, preferably in the range of about 45 psi to about 1000 psi, and most preferably in the range of about 45 psi to about 250 psi.

Although the residence time of the reactants in the reactor or alkylation zone can vary widely depending upon the process variables, the residence time is generally in the range of about 0.01 minutes to about 100 minutes. Preferably, the residence time is in the range of about 0.1 minutes to about 30 minutes, and more preferably in the range of about 1 minutes to about 20 minutes, and most preferably in the range of about 5 minutes to about 20 minutes.

EXAMPLES

Experiments were conducted to evaluate the present invention. For the experiments, the typical olefin space velocity was about 0.3/hr, which corresponds to about 13 minutes of residence time when the reactor contains 53 volume percent acid and with the typical amount of propane and n-butane in the combined feed stream to the reactor. Other conditions include alkylation temperature of about 50° F., and an isobutane to olefin molar ratio of about 8, and unless otherwise stated, an average sulfuric acid strength of about 94 weight percent.

The mixed butylene or mixed amylene feed utilized below were prepared to represent typical distribution of olefin isomers that would be found in a refinery feed stream. Isobutane was utilized as the isoparaffin.

Figure 17:
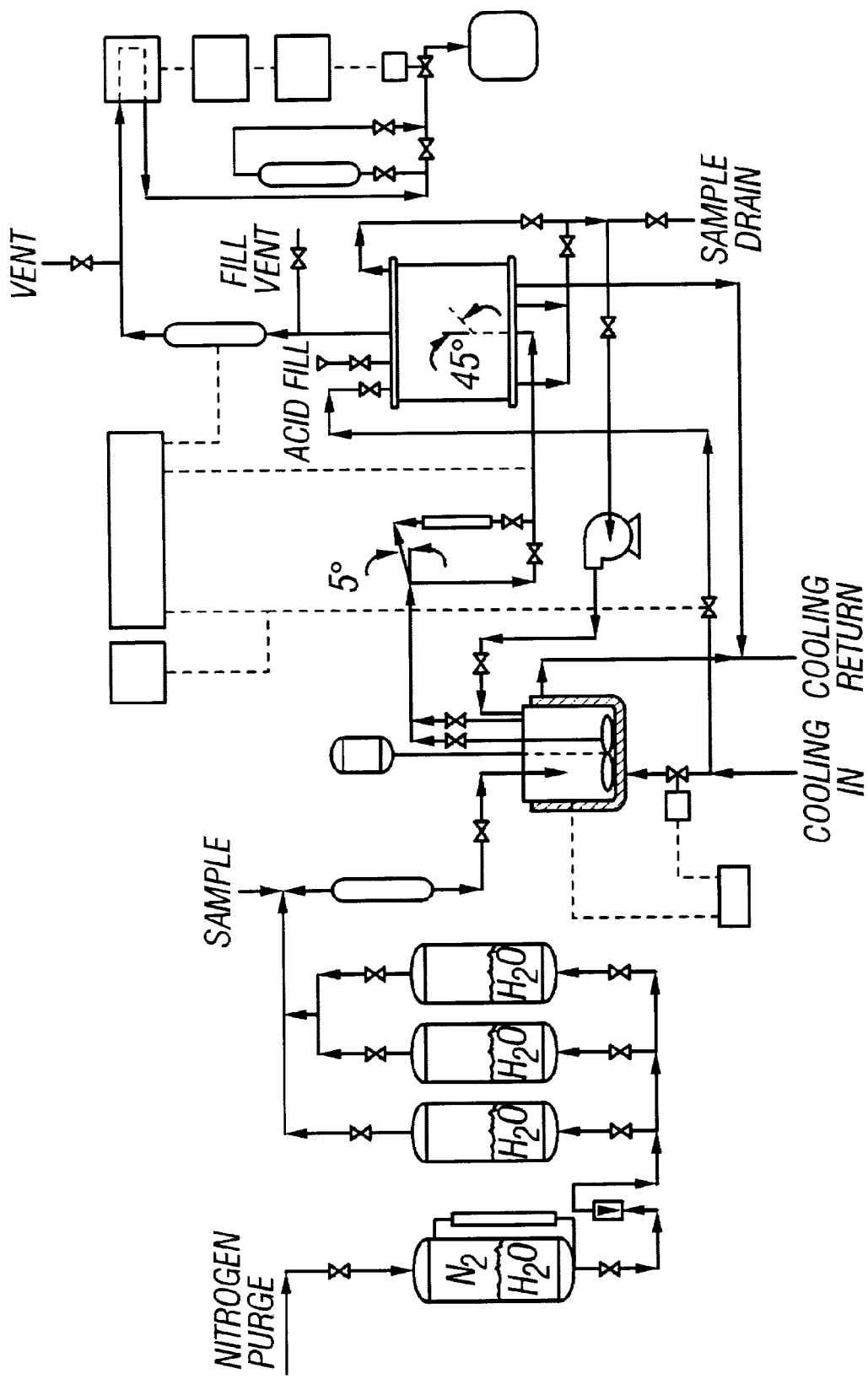
FIG. 17 is a schematic of the bench scale equipment utilized in these Examples, showing water cylinder 1, water flowmeter 2, fill isobutane 3, isoparaffin and olefin feed cylinder 4, molecular sieve 5, variable speed motor 6, 450 ML reactor 7, temperature readout controller 8, I-P valve actuator 9, temperature controller 10, multi-point temperature recorder 11, emulsion sight glass 12, variable speed acid recycle pump 13, caustic bed 14, glass settler 15, effluent sample cylinder 16, flowmeter 17, transmitter with totalizer 18, flow controller 19, I-P valve actuator 20, and product vessel 21.

Bench scale equipment, as schematically represented in FIG. 17, was used for this study. FIG. 17 is a schematic of the bench scale equipment utilized in these Examples, showing water cylinder 1, water flowmeter 2, fill isobutane 3, isoparaffin and olefin feed cylinder 4, molecular sieve 5, variable speed motor 6, 450 ML reactor 7, temperature readout controller 8, I-P valve actuator 9, temperature controller 10, multi-point temperature recorder 11, emulsion sight glass 12, variable speed acid recycle pump 13, caustic bed 14, glass settler 15, effluent sample cylinder 16, flowmeter 17, transmitter with totalizer 18, flow controller 19, I-P valve actuator 20, and product vessel 21.

The mixer speed for reactor 7 is maintained at about 1100 rpm. Five gallon water cylinder 1 was pressured to approximately 120 psi with nitrogen. The water flows from the water cylinder 1 through flowmeter 2 and into the bottom of cylinder 4 mixed isobutane/olefin feed. The hydrocarbon feed was fed through molecular sieve 5 to remove water from the feed, and then into the reactor 7. Effluent was drawn off the bottom of the reactor 7 and then directed into the settler 15. Acid is drawn from the bottom of the settler 15 and recirculated back to the reactor 7. The hydrocarbon product flows from the top of the settler 15 through caustic bed 14, and into the product cylinder 21.

A "stock" supply of synthetic low-strength acid was generated as follows. The olefins are sparged into a volume of fresh, water-white acid (98.5–99 wt % $H_2SO_4$). The acid is kept at a temperature no more than 100° F. to minimize extended polymerization of the forming acid-soluble oils. Samples of the acid are analyzed periodically to determine the diluted acid strength. When the acid reaches approximately 90 wt % $H_2SO_4$, the hydrocarbon flow is stopped and the acid is refrigerated until needed. Knowing the weight percent of the fresh and synthetic acids, it is possible to mix calculated amounts of the fresh and "stock" synthetic acids together to form a volume of specific strength acid. Using a similar technique, non-synthetic spent acid-removed from the pilot plant at the end of an experiment-can be "boosted" to a target strength with the calculated volume of fresh acid (98.5–99 wt % $H_2SO_4$). This technique is used when a series of experiments utilizing the same (or effectively similar) feed is run over the course of a few days. This technique cuts down on waste acid and has no noticeable side effects as long as the feed composition remains constant or consistent.

Alternatively, some synthetic used sulfuric acid was prepared by first spiking fresh acid with oleum to raise the acidity to 98.5–99% $H_2SO_4$. Butene-1 was then bubbled through the acid until the acidity is reduced to approximately 97.5% $H_2SO_4$. Then 2-butenes are bubbled through the acid until an acidity of 94.5–95% $H_2SO_4$ is obtained.

The system described was then charged with 500 ML of synthetic used acid prepared as directed. An average acid to hydrocarbon volume ratio in the reactor of 45 to 65% was maintained throughout the runs. Usually the acid to hydrocarbon ratio was maintained at 50–55% (v/v). The settler temperature was monitored at the bottom of the settler and where the hydrocarbon effluent exits. The temperature of effluent was kept at about the reactor temperature while the temperature of the acid exiting the settler is maintained at or below the reactor temperature.

A sample of acid and product was analyzed about every 1.5 hours. To eliminate start-up effects, the first data point was taken at the 1.5 hour point. The acid was sampled by first purging 5 ML of acid through a sampling valve followed by collecting an additional 5 ML in a centrifuge tube. The acid sample was then centrifuged for 15 minutes and about 0.5 g (weighed to +/−0.1 mg) was titrated to 5.8 pH methyl red end point with standardized aqueous NaOH. The alkylate samples were analyzed by a standard gas chromatograph (G.C.) procedure. The G.C. was equipped with a 50 m capillary column which could separate hydrocarbons up to $C_{14}$.

Using the previously described reaction scheme, the following Examples were conducted.

Examples 1–3 compare alkylation of a combined feed (Example 1), to alkylation of olefins separately (Example 2), to alkylation of propylene separately (Example 3). Unless stated otherwise, Examples 1–3 were carried out at same conditions.

Example 1

A 39/41/20 (vol %) propylene/MTBE ("methyl tertiary butyl ether") raffinate/TAME ("tertiary amyl methyl ether") raffinate feed was alkylated at 45° F., an olefin space velocity of 0.38/hour, and an isobutane:olefin molar ratio of 9. The feed was divided into 10 runs and processed through the Experimental apparatus as described above. The true alkylate octane for the 10 runs averaged 90.5 (R+M)/2.

Example 2

Same as Example 1, except that 4 runs of propylene feed was alkylated at an acidity of 93% $H_2SO_4$, olefin space velocity of 0.41, and an $iC_4$/Olefin ratio of 7, 4 runs of MTBE raffinate was alkylated at an acidity of 93% $H_2SO_4$, olefin space velocity of 0.38, and an $iC_4$/Olefin ratio of 9.5, and 2 runs of TAME raffinate was alkylated at an acidity of 90% $H_2SO_4$, olefin space velocity of 0.22, and an $iC_4$/Olefin ratio of 13.5. All olefins were reacted at a reaction temperature of 45° F., and the alkylates from all three olefin types were combined in proportion to the amount of olefin in the feed and the yield of each olefin. The blended true alkylate octane was 91.4 (R+M)/2, which is nearly an octane number increase over that of Example 1.

Example 3

Same as Example 1, except that 5 runs of propylene feed was alkylated at an acidity of 94–95% $H_2SO_4$, olefin space velocity of 0.27, an $iC_4$/Olefin ratio of 7.6, at 60° F., and 6 runs of the MTBE raffinate/TAME raffinate mixture was alkylated at an acidity of 92% $H_2SO_4$, olefin space velocity of 0.36, and an $iC_4$/Olefin ratio of 10, at 45° F. The blended true octane number was 92.9 (R+M)/2, which is 1.5 octane numbers higher than Example 2, and 2.4 octane numbers higher than Example 1, which seems to indicate that alkylating propylene at higher reaction temperatures and lower olefin space velocities will increase alkylate octane numbers.

Example 4

Propylene, mixed $C_4$s and mixed $C_5$s were each alkylated for a few hours with isobutane. Between 3–4.5 hours, the olefin feed was stopped and only isobutane was fed to the reactor. This, in effect, "washed" the acid with isobutane to react any remaining alkyl sulfate esters.

Experimental data is presented in FIG. 1 which is a graph of acid strength versus run time showing the effect of an isobutane wash for various olefin feeds. FIG. 1 shows that there is a large "washing" effect only for propylene. The acid strength can increase greatly when propylene are no longer being introduced to the reactor. With acid just used with mixed $C_4$ or mixed $C_5$ olefins, the rise in acid strength was barely detectable (0.2 wt % $H_2SO_4$). For propylene acid, a number of hours were required to completely react the propyl sulfate esters with isobutane.

Example 5

Propylene was alkylated with isobutane until the reaction would reach an acid runaway, at which point, the acid was washed by switching the isobutane/propylene feed to an isobutane/$C_4$ olefin feed when the acid dropped below 88 wt % $H_2SO_4$. Surprisingly, the acid strength rose dramatically, nearly reaching the starting strength within 1.5 hours of the feed switch. The experiment was repeated by allowing the acid strength to decrease to about 86 wt % $H_2SO_4$ before switching to the isobutane/$C_4$ olefin feed. The experimental results are presented in FIG. 2 which is a graph of weight percent sulfuric acid versus run time showing the effect of a mixed butylene feed for washing propylene acid.

Figure 2:
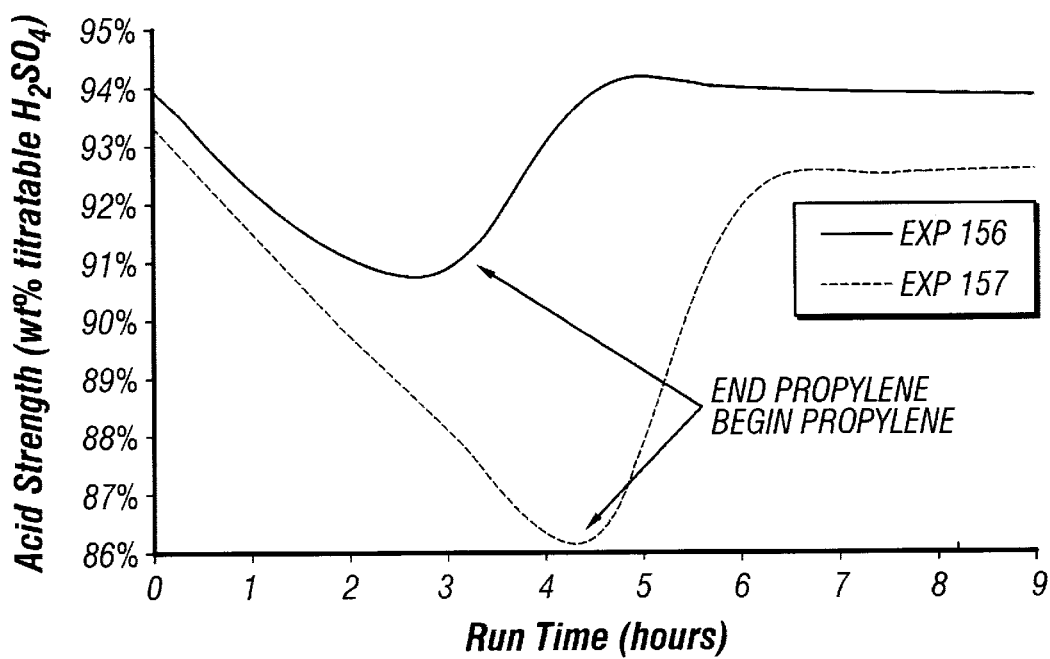
FIG. 2 is a graph of weight percent sulfuric acid versus run time showing the effect of a mixed butylene feed for washing propylene acid.
Figure 3:
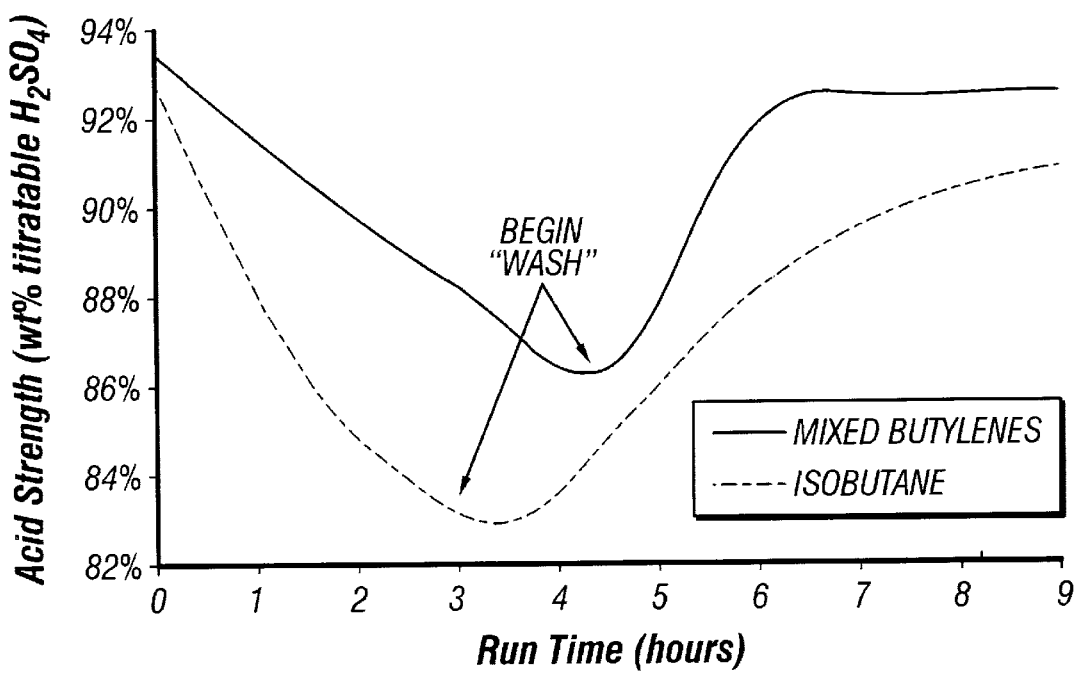
FIG. 3 is a graph of the acidity change when the acid during propylene alkylation is "washed" with isobutane (from FIG. 1) or "washed" with a mixed butylene feed (from FIG. 2).

FIG. 3 is a graph of the acidity change when the acid during propylene alkylation is "washed" with isobutane (from FIG. 1) or "washed" with a mixed butylene feed (from FIG. 2). As shown in FIG. 3, washing the propylene acid with an isobutane/$C_4$ olefin feed increases the acid strength much more quickly than washing with isobutane alone. While the isobutane washing does start at a lower acid strength, a comparison of the change in acid strength at 86% or above (i.e., the slope of the line), shows the benefit of the isobutane/$C_4$ olefin feed.

Example 6

This example compares acidity decline in the alkylation of propylene utilizing acids which have been previously used to alkylate either propylene or amylenes.

FIG. 3 compared the difference between washing the acid with either isobutane or an i$C_4$/$C_4$ olefin feed. At the "begin wash" point in FIG. 3, the olefin feed to the alkyation reaction was ceased, and only isobutane feed to the alkylation reaction. While the starting acidity for these two experiments was similar, the decline in acidity was much greater for one than for the other. The difference was found to be in the history of the acid, or the type of acid soluble oils that have formed.

The least acidity decline occurred utilizing acid which had only been used with high content propylene (or all propylene) feeds. Using acid previously utilized to alkylate feeds having large amounts of or exclusively $C_5$ olefins (amylenes), resulted in a very rapid drop in acidity. While not wishing to be limited to theory, the inventors believe that since the amount of water in the acids is relatively constant, the reason for the difference is probably due to the nature of the acid soluble oils. This indicates that if propylene and amylenes are being alkylated in separate reactors with the acid flowing in series between the reactors, propylene should be reacted first. Feeding acid from a reactor alkylating amylenes into a reactor alkylating propylene could result in higher acid consumption.

Figure 4:
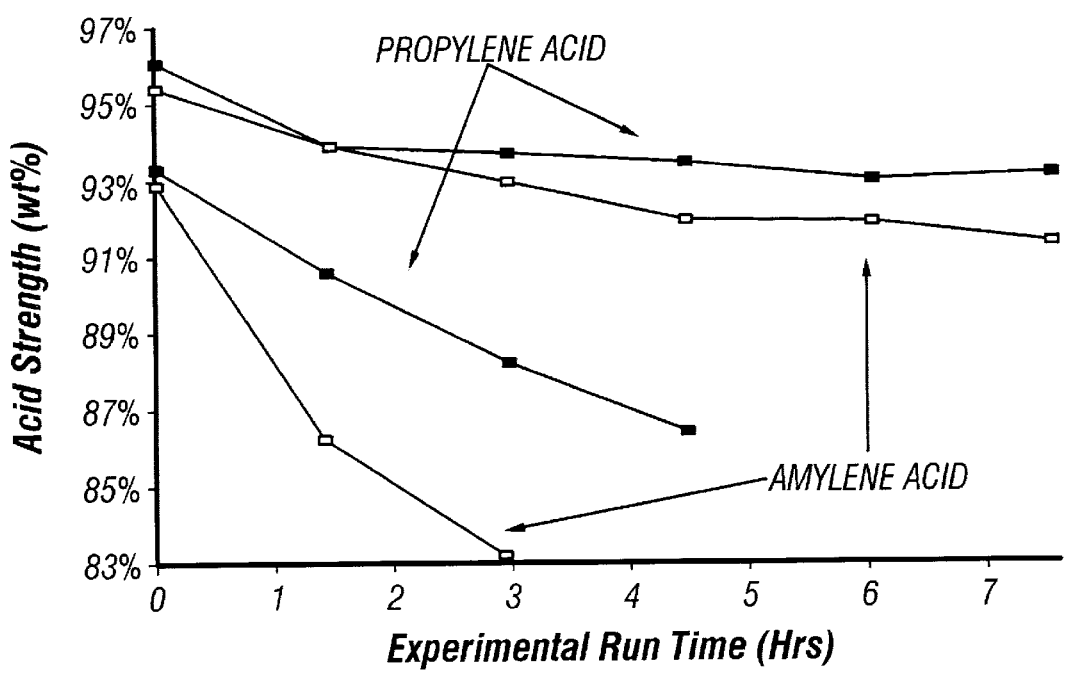
FIG. 4 is a graph of acid strength versus run time for the alkylation of propylene with an acid previously used to alkylate either propylene or amylenes.

In this Example, propylene was alkylated with acid which was previously used to alkylate either propylene or amylenes. Results of this Example are presented in FIG. 4 which is a graph of acid strength versus run time for the alkylation of propylene with an acid previously used to alkylate either propylene or amylenes.

Subsequent experiments have shown that acid used with either propylene or $C_4$ olefin feeds perform satisfactory when used to alkylate propylene.

Example 7

Isobutane was alkylated with a 100% propylene feed at various alkylation temperatures. About 7.5 hours into the alkylation, the propylene feed was replaced by a $C_4$ olefin feed at 50° F. Results are presented in FIGS. 5–8.

Figure 5:
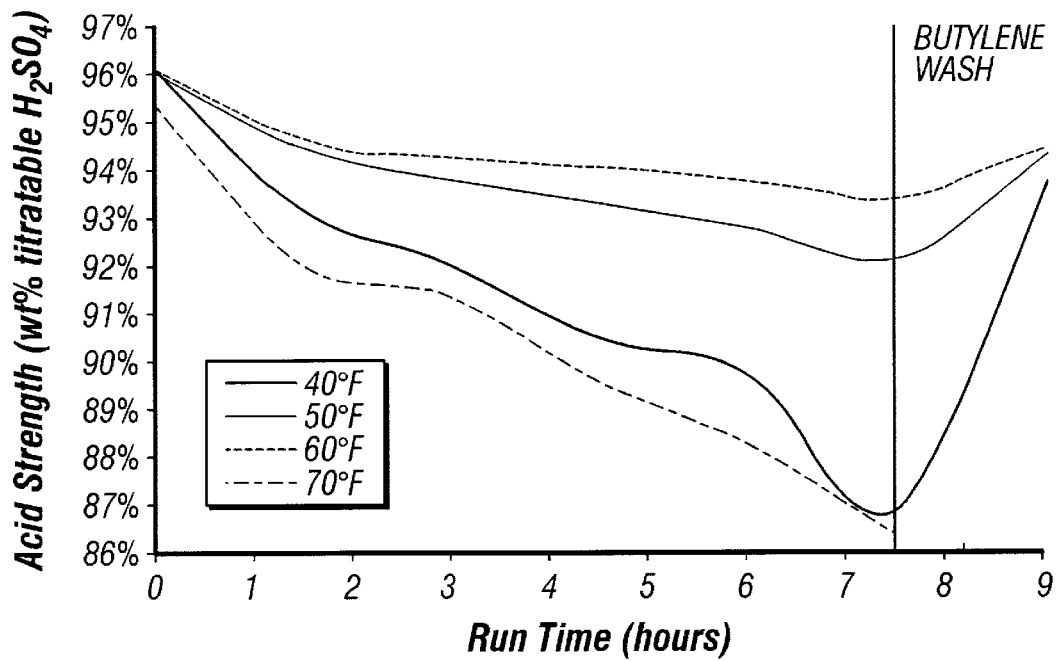
FIG. 5 is a graph of acid concentration versus run time for the alkylation of isobutane with propylene at various alkylation temperatures.

FIG. 5 is a graph of acid concentration versus run time for alkylation of isobutane with propylene at various alkylation temperatures. Lower reaction temperatures appear to result in a less complete reaction. Higher reaction temperatures result in less of an acidity increase when washed with $C_4$ olefins, indicating a more complete reaction.

Figure 6:
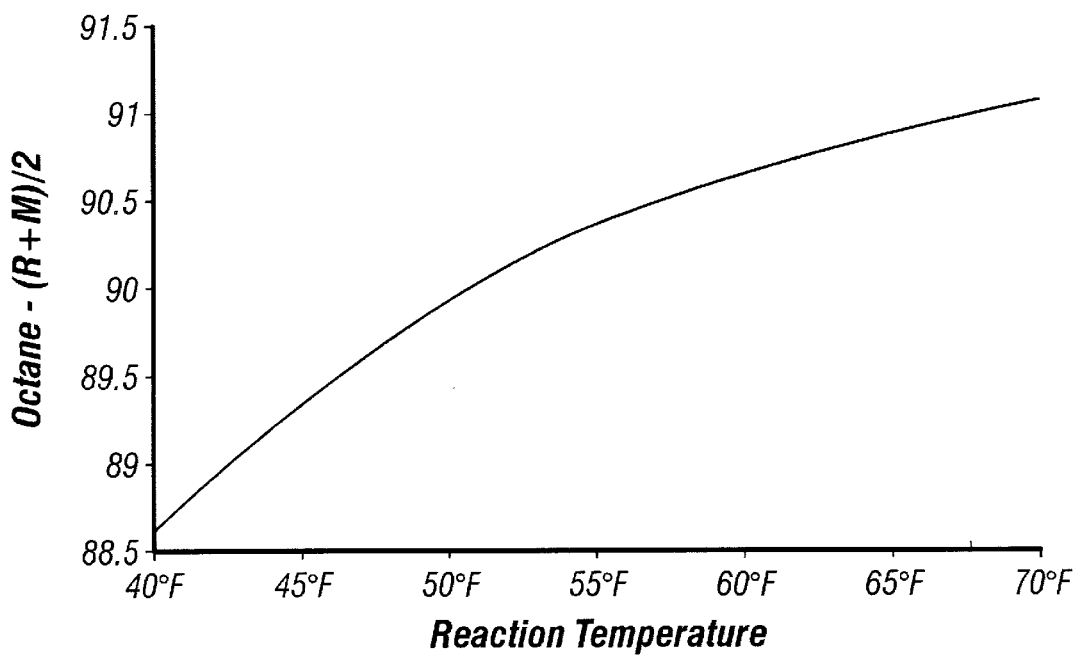
FIG. 6 is a graph of octane number versus reaction temperature for alkylation of isobutane with propylene at various alkylation temperatures, showing an increase of octane number with increasing alkylation temperature.

FIG. 6 is a graph of octane number versus reaction temperature for alkylation of isobutane with propylene at various alkylation temperatures, showing an increase of octane number with increasing alkylation temperature.

Figure 7:
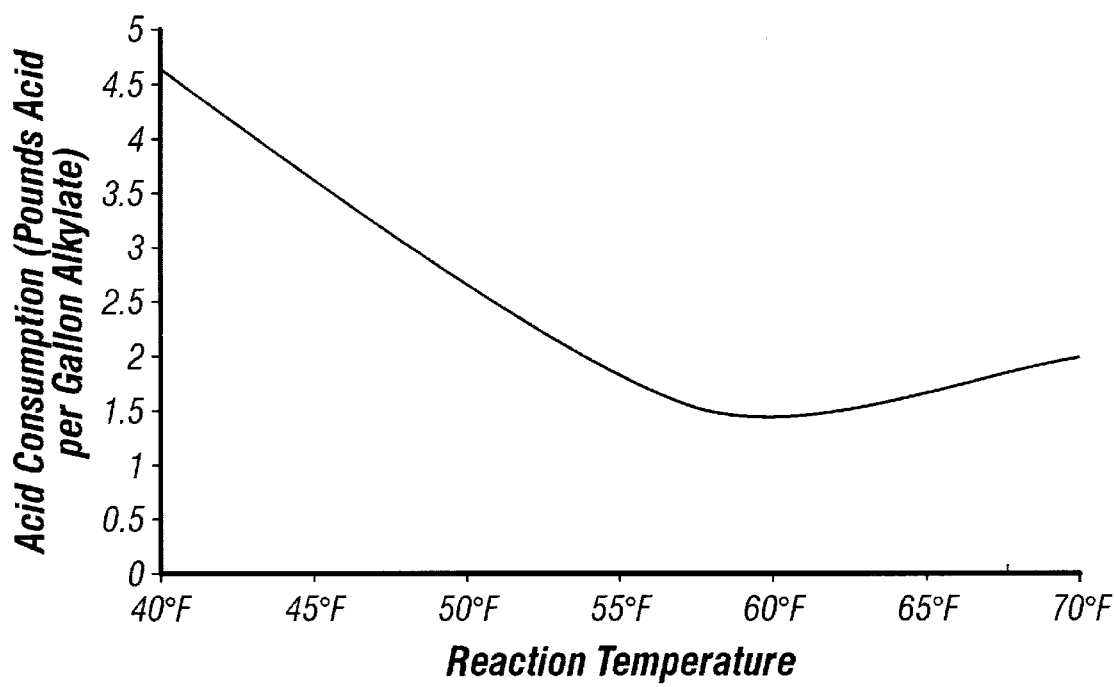
FIG. 7 is a graph of acid consumption versus reaction temperature for alkylation of isobutane with propylene at various alkylation temperatures, showing a decrease of acid consumption from 40° F. to 60° F., and an increase of acid consumption above 60°.

FIG. 7 is a graph of acid consumption versus reaction temperature for alkylation of isobutane with propylene at various alkylation temperatures, showing a decrease of acid consumption from 40° F. to 60° F., and an increase of acid consumption above 60°.

Figure 8:
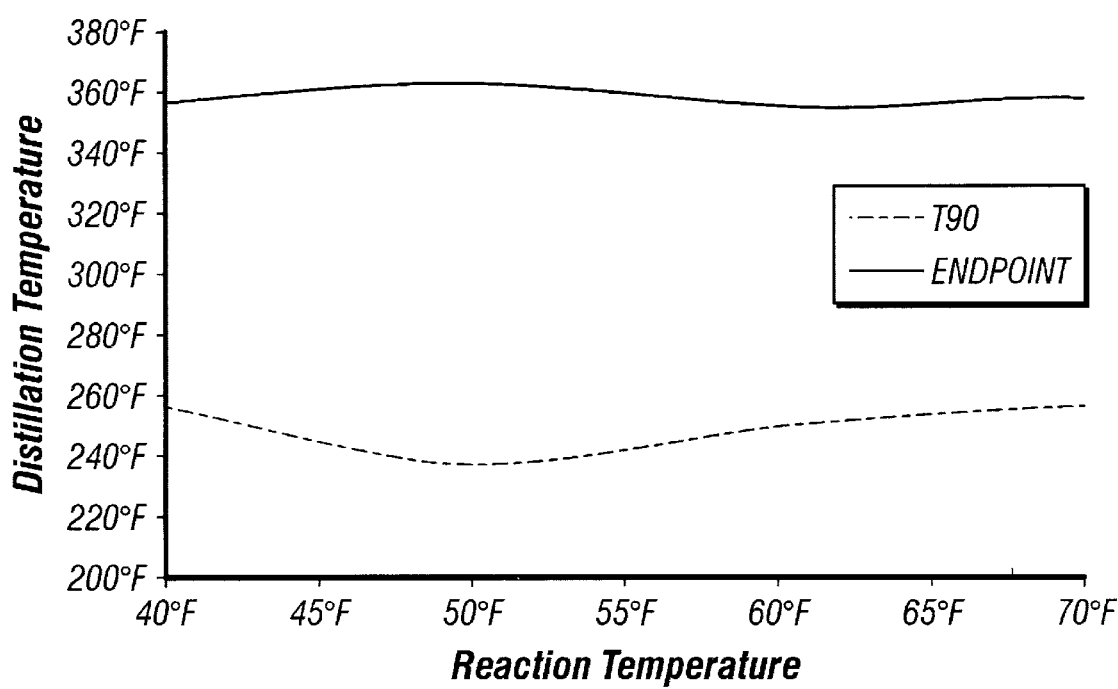
FIG. 8 is a graph of ASTM D-86 distillation T90 and End Point data for alkylation of isobutane with propylene at various alkylation temperatures, showing only a minor effect upon the T90 and End Point data with varying alkylation temperature.

FIG. 8 is a graph of ASTM D-86 distillation T90 and End Point data for alkylation of isobutane with propylene at various alkylation temperatures, showing only a minor effect upon the T90 and End Point data with varying alkylation temperature.

Example 8

Isobutane was alkylated with a 100% propylene feed at various olefin space velocities. About 7.5 hours into the alkylation, the propylene feed was replaced by a $C_4$ olefin feed at an olefin space velocity of 0.3/hr. Results are presented in FIGS. 9–10.

Figure 9:
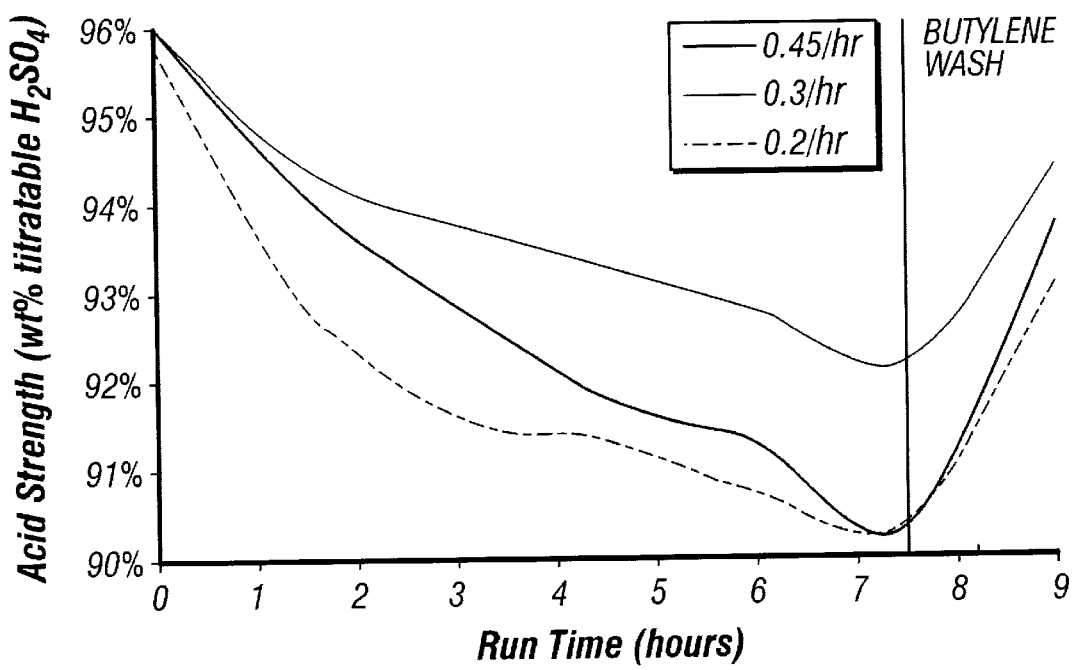
FIG. 9 is a graph of acid concentration versus run time for alkylation of isobutane with propylene at various olefin space velocities. Higher olefin space velocities appear to result in a less complete reaction. Lower space velocities result in less of an acidity increase when washed with $C_4$ olefins, indicating a more complete reaction.

FIG. 9 is a graph of acid concentration versus run time for alkylation of isobutane with propylene at various olefin space velocities. Higher olefin space velocities appear to result in a less complete reaction. Lower space velocities result in less of an acidity increase when washed with $C_4$ olefins, indicating a more complete reaction.

Figure 10A:
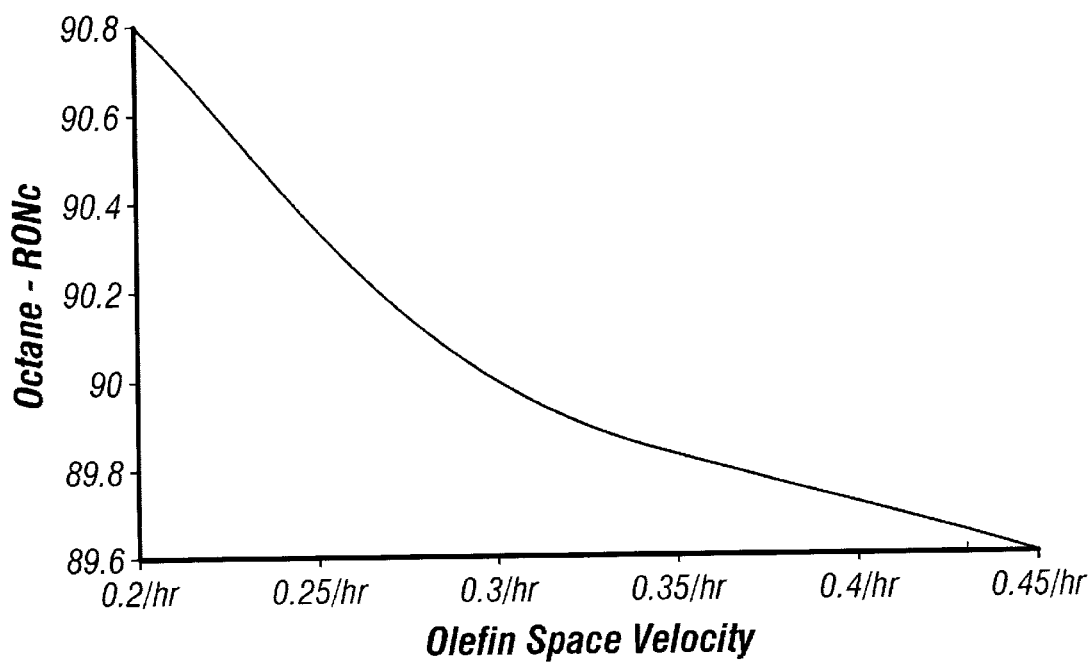
FIG. 10A and FIG. 10B are graphs, respectively, of octane number, and ASTM D-86 distillation T90 and End Point data for alkylation of isobutane with propylene at various olefin space velocities, showing only a minor effect upon the T90 and End Point data with varying alkylation temperature, and a decrease of octane number as the olefin space velocity increases from 0.2/hr to 0.45/hr.
Figure 10B:
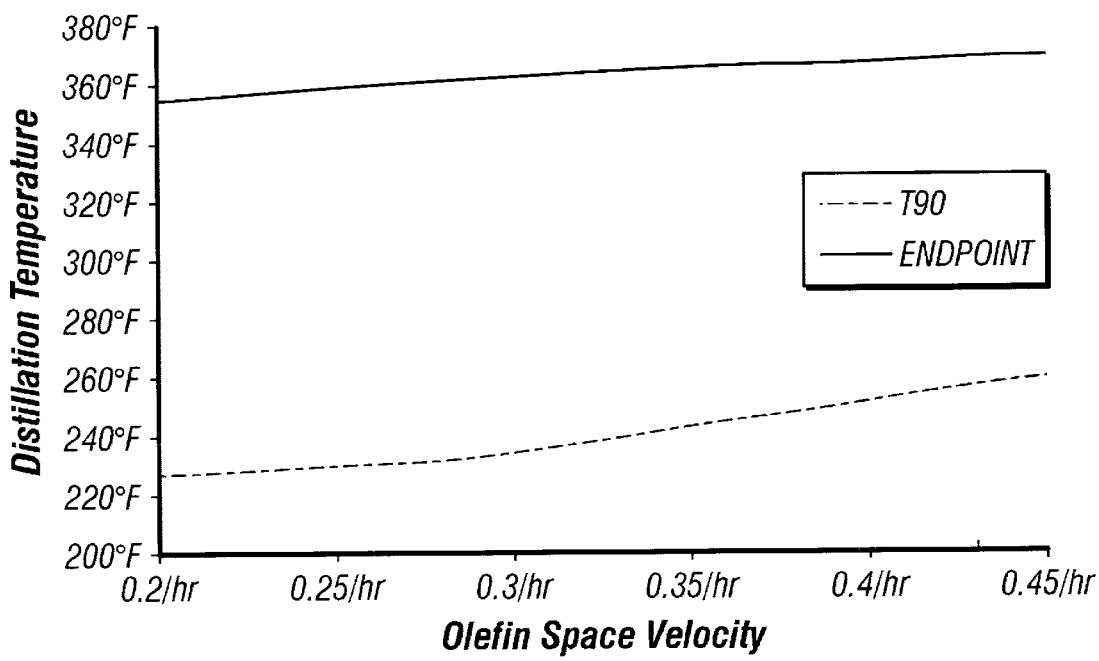

FIG. 10 is a graph of octane number, and ASTM D-86 distillation T90 and End Point data for alkylation of isobutane with propylene at various olefin space velocities, showing only a minor effect upon the T90 and End Point data with varying alkylation temperature, and a decrease of octane number as the olefin space velocity increases from 0.2/hr to 0.3/hr.

Example 9

Figure 11:
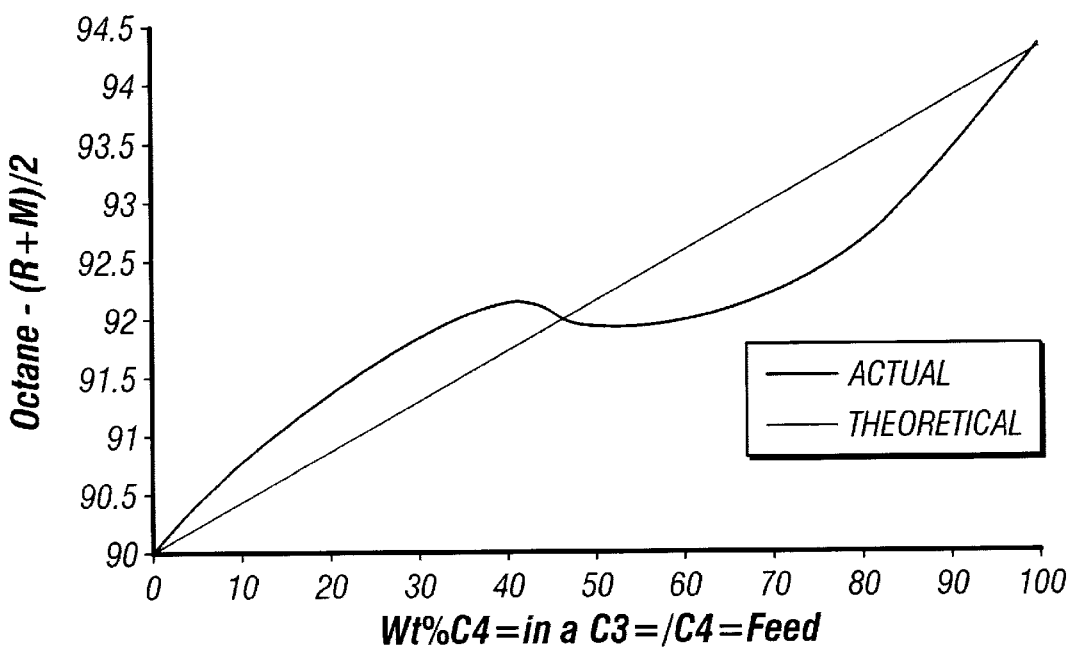
FIG. 11 is a graph of octane number versus weight percent $C_3$ olefin in a $C_3/C_4$ olefin feed for both actual data and predicted results, showing that above about 55 weight percent $C_3$ olefin, higher than expected octane numbers are obtained, and showing that below about 55 weight percent $C_3$ olefin lower than expected octane numbers are obtained.
Figure 12:
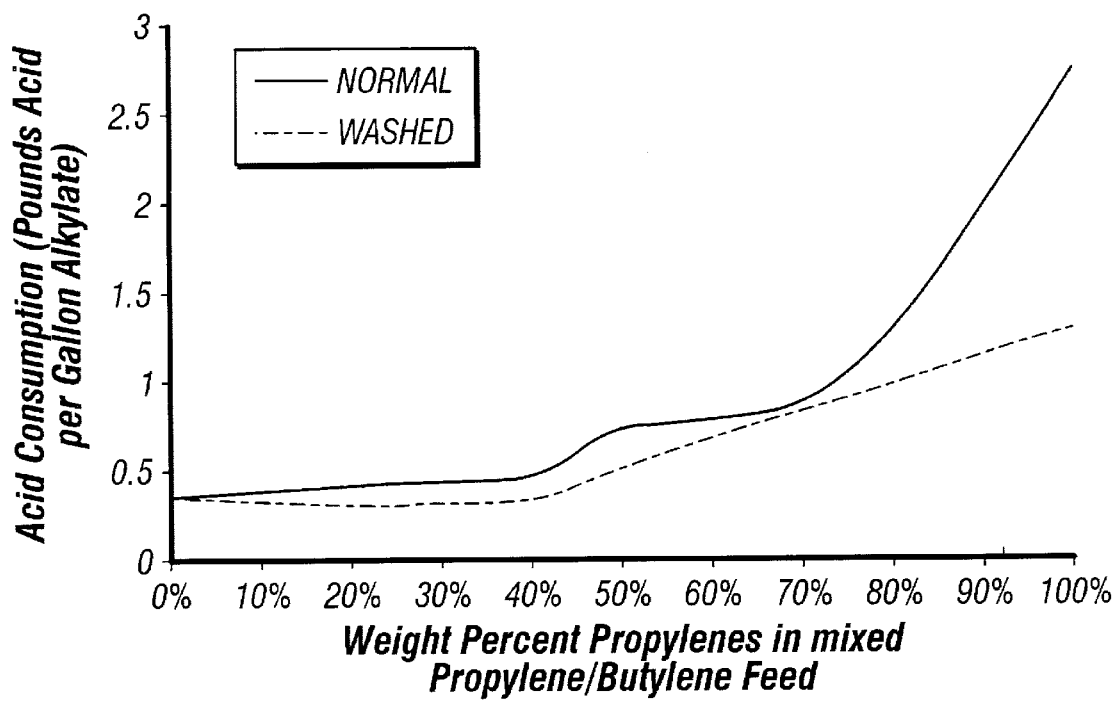
FIG. 12 is a graph of acid consumption (pounds acid/ gallons alkylate produced) versus weight percent propylene in a $C_3/C_4$ olefin feed, showing a trend of increasing acid consumption above about 40 weight percent propylene in the feed.

Isobutane was alkylated with $C_3$ and $C_4$ olefins at various $C_3$/$C_4$ olefin ratios. Results are presented in FIG. 11 and FIG. 12. FIG. 11 is a graph of octane number versus weight percent $C_4$ olefin in a $C_3$/$C_4$ olefin feed showing both actual data, and predicted results. Below about 45 weight percent $C_4$ olefin higher than expected octane numbers are obtained, and showing that above about 45 weight percent $C_4$ olefin lower than expected octane numbers are obtained. FIG. 12 is a graph of acid consumption (pounds acid/gallons alkylate produced) versus weight percent propylene in a $C_3$/$C_4$ olefin feed, showing a trend of increasing acid consumption about 40 weight percent propylene in the feed.

Example 10

Figure 13:
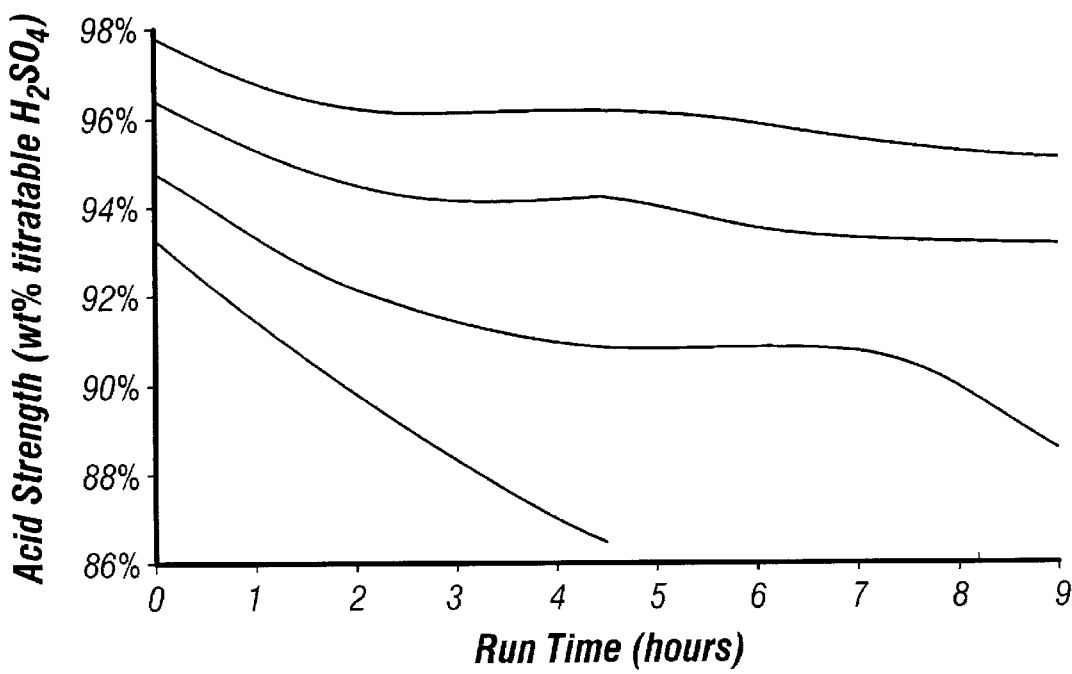
FIG. 13 is a graph of weight percent sulfuric acid versus experiment run time, for the alkylation of isobutane with 100% propylene at various starting acid strengths, showing greater rates of acid strength declines at lower starting acid strengths.

This Example shows the effect the strength of the starting acid has on the acidity decline during a typical experiment. The runs were initially started with 98% reagent grade sulfuric acid. At the end of each day, fresh acid was added to maintain the 500 ml starting acid volume. Thus, the strength of the acid charged back into the pilot plant apparatus the next day was increased slightly. Results are presented in FIG. 13, which is a graph of weight percent sulfuric acid versus experiment run time, for the alkylation of isobutane with 100% propylene at various starting acid strengths, showing greater rates of declines in acidities at lower starting acid strengths. When the acidity reached about 92% $H_2SO_4$, the first stages of an acid runaway were occurring. This indicates for alkylation feeds containing large amounts of propylene, the acidity should be maintained at higher spending strengths. Or, in the case of alkylating the olefins and alkylating then at different stages, propylene should be fed into the reactor with the highest acidity (generally the first).

Example 11

Figure 14:
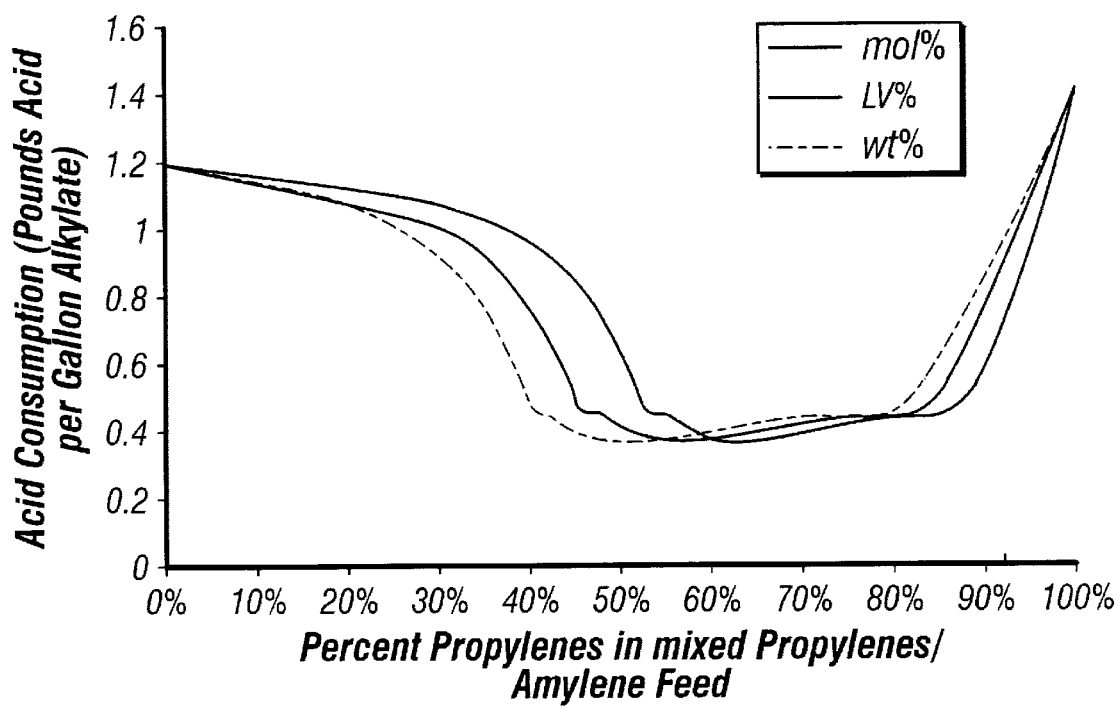
FIG. 14 is a graph of acid consumption versus percent propylene in a $C_3$/mixed $C_5$ olefin feed for alkylation of isobutane.
Figure 15:
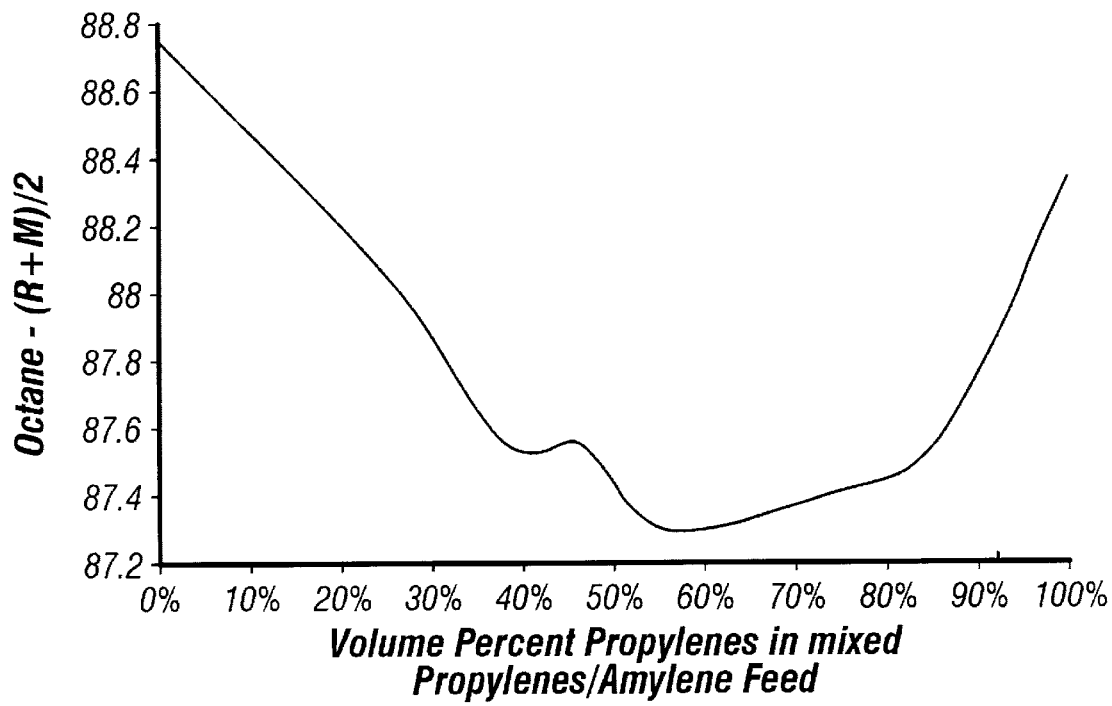
FIG. 15 is a graph of octane number versus percent propylene in a $C_3$/mixed $C_5$ olefin feed for alkylation of isobutane.
Figure 25:
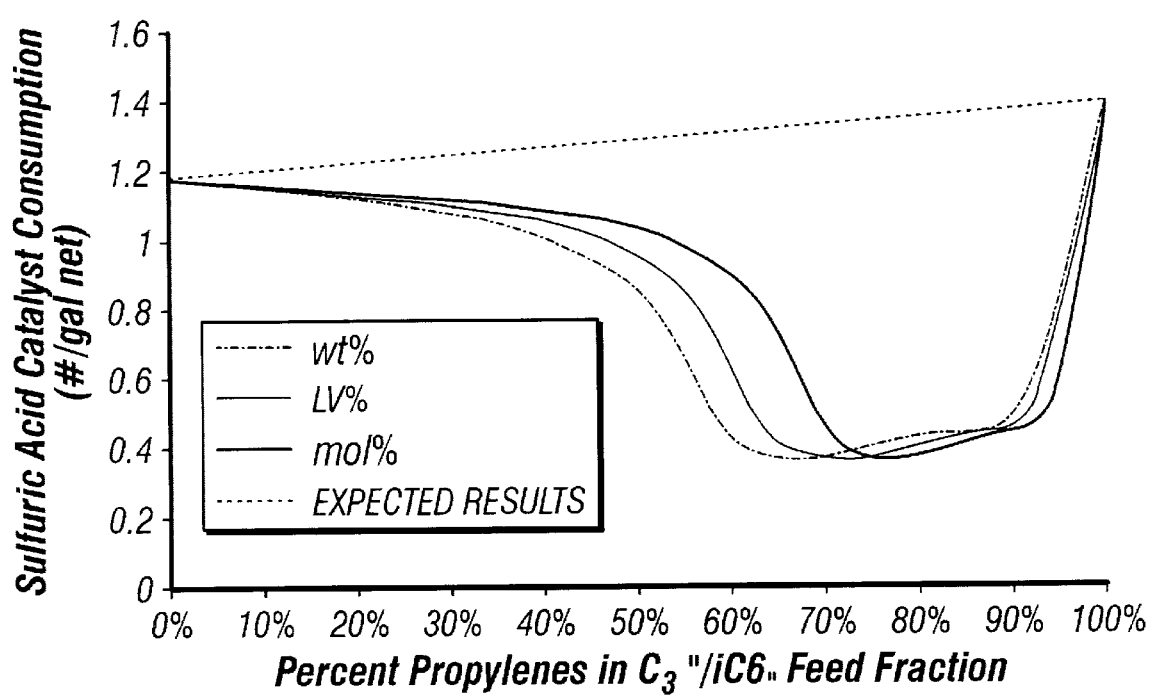
FIG. 25 is a graph of acid consumption versus percent propylene in a $C_3$/iso-$C_5$ olefin feed for alkylation of isobutane.

Isobutane was alkylated with a propylene/amylenes feed at various propylene/amylene ratios. Results are presented in FIGS. 14, 15 and 25. FIG. 14 is a graph of acid consumption versus percent propylene in a $C_3$/mixed $C_5$ olefin feed for alkylation of isobutane. FIG. 15 is a graph of octane number versus percent propylene in a $C_3$/mixed $C_5$ olefin feed for alkylation of isobutane. FIG. 25 is a graph of acid consumption versus percent polypropylene in a $C_3$/iso-$C_5$ olefin feed for alkylation of isobutane. As shown in FIG. 14, $C_3$/mixed $C_5$ olefin feed mixtures consume less acid than either olefin alone for almost the entire range. The three curves in FIG. 14 represent the same data, only presented in different units. Typically, about half of the $C_5$ olefins are iso-olefins such as methyl-2-butene. Of course, the ratio of iso to linear $C_5$ olefins vary somewhat depending on how much of the $C_5$ olefin stream is recovered for alkylation. While not being limited by theory, the inventors believe that the iso-$C_5$ olefins are greatly, if not prdominately, substantially, or fully responsible for the improved acid consumption. As shown in FIG. 25, $C_3$/iso-$C_5$ feed mixtures consume less acid than either olefin alone for for almost the entire range. The three lower curves in FIG. 25 represent the same data in different units with fourth dashed curve expressing the expected acid consumption results. The preferred range of propylene to iso-amylene to reduce acid consumption is therefore between about 45 and about 95% LV. As shown in FIG. 15, there is an octane penalty when utilizing a $C_3$/mixed $C_5$ olefin feed for alkylation of isobutane, which penalty must be weighed against the acid consumption savings.

Example 12

Figure 16:
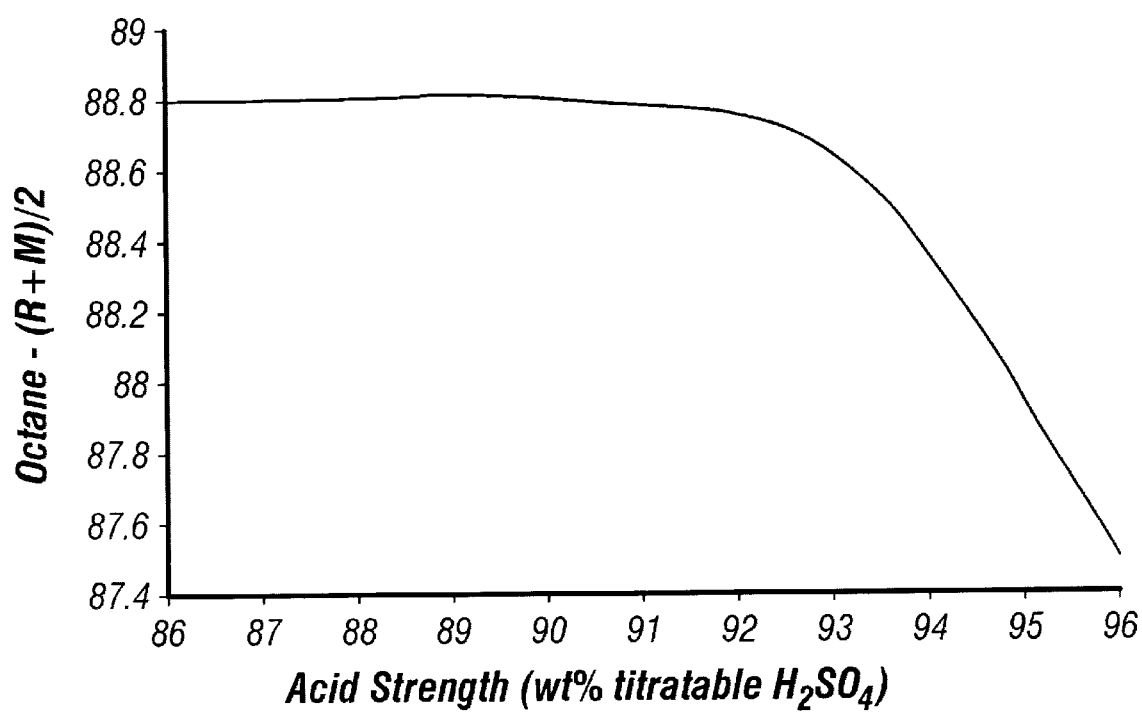
FIG. 16 is a graph showing the effect of acidity on alkylate product octane for an amylene feed.

Isobutane was alkylated with amylenes sulfuric acid catalysts of various acid strengths. Results are presented in FIG. 16. FIG. 16 is a graph of alkylate octane number versus acid strength for the alkylation of amylene and isobutane. As shown, in the range from about 93 to about 86.5%, the alylate octane number is generally constant.

Example 13

Isobutane was alkylated with various olefins to examine the effect of reaction temperature, olefin space velocity or isobutane/olefin ratio on octane or acid consumption. Results are presented in FIGS. 18–23.

Figure 18:
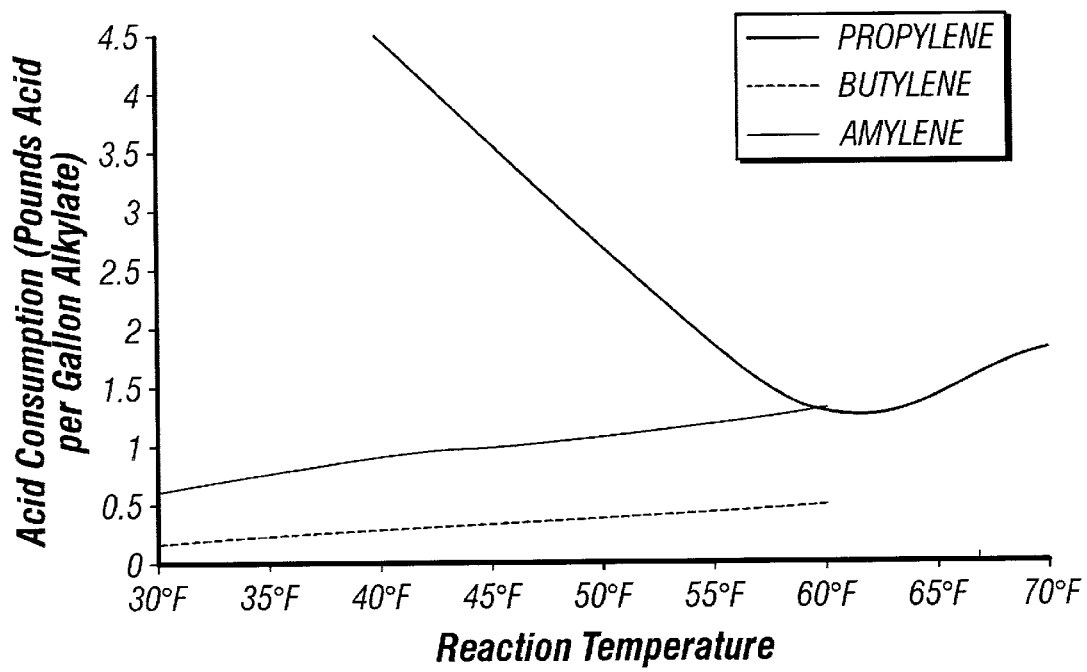
FIG. 18 is a graph showing the relationship between acid consumption and reaction temperature for propylene, butylenes and amylenes.
Figure 19:
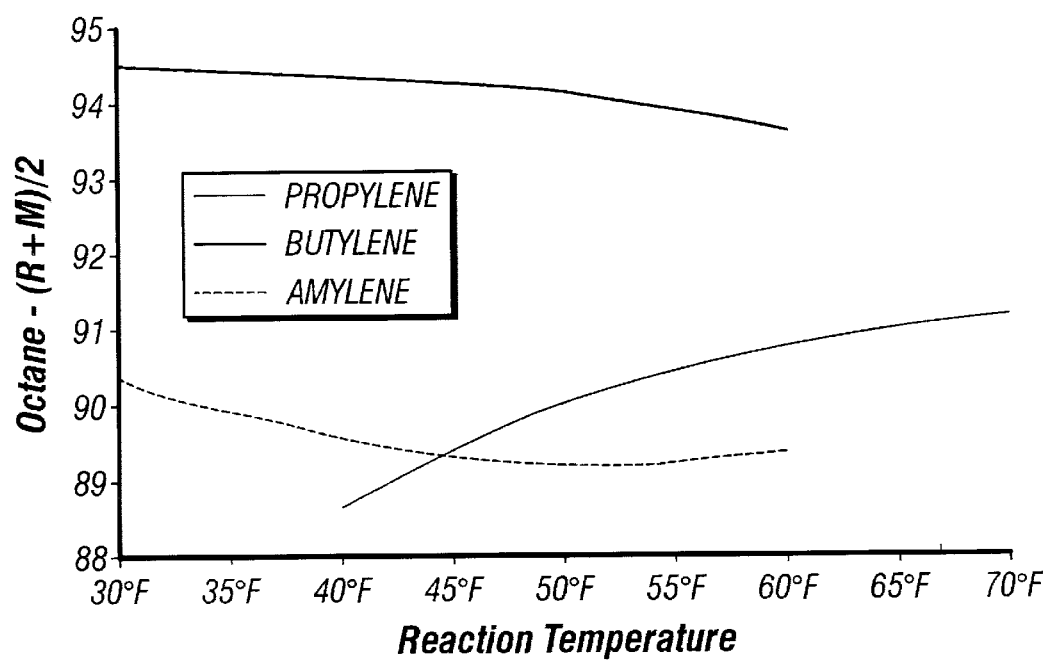
FIG. 19 is a graph showing the relationship between alkylate product octane number and alkylation reaction temperature for propylene, butylenes and amylenes.

FIGS. 18 and 19 are graphs which show the effect of alkylation temperature on acid consumption and alkylate octane, respectively.

Figure 20:
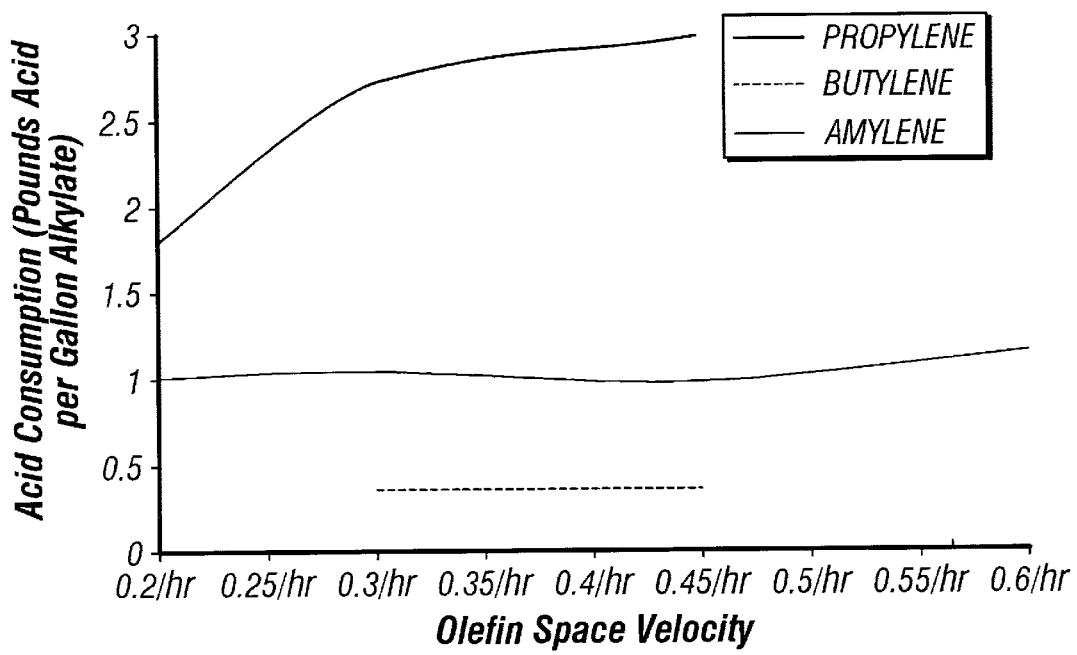
FIG. 20 is a graph showing the relationship between pounds acid consumption per gallons of net alkylate product produced and olefin space velocity.
Figure 21:
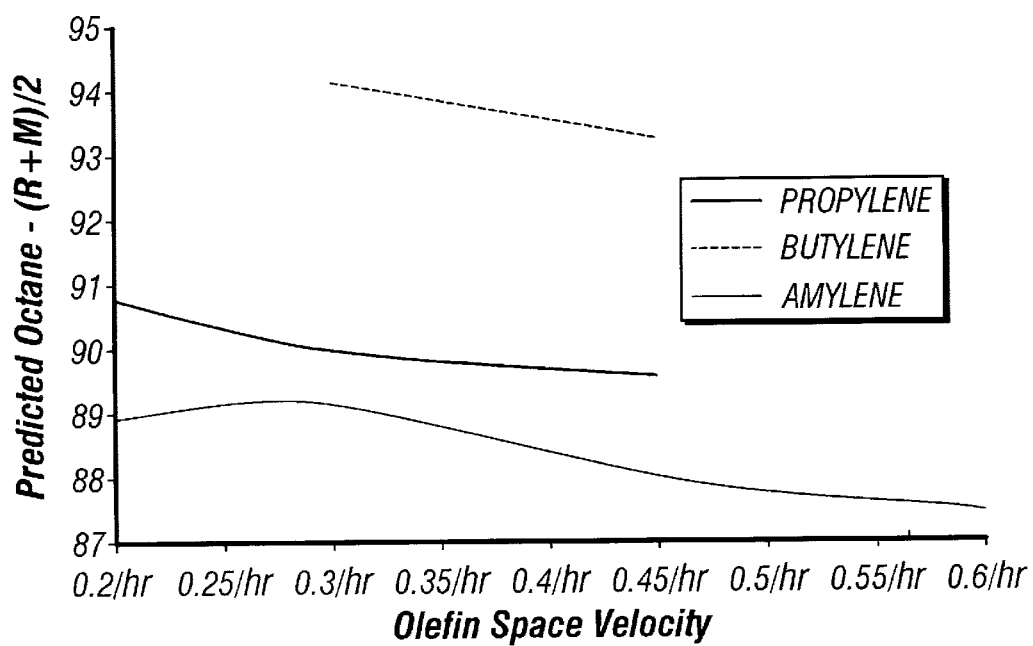
FIG. 21 is a graph showing the relationship between octane number of the alkylate product produced and olefin space velocity.

FIGS. 20 and 21 are graphs which show the effect of olefin space velocity on acid consumption and alkylate octane, respectively.

Figure 22:
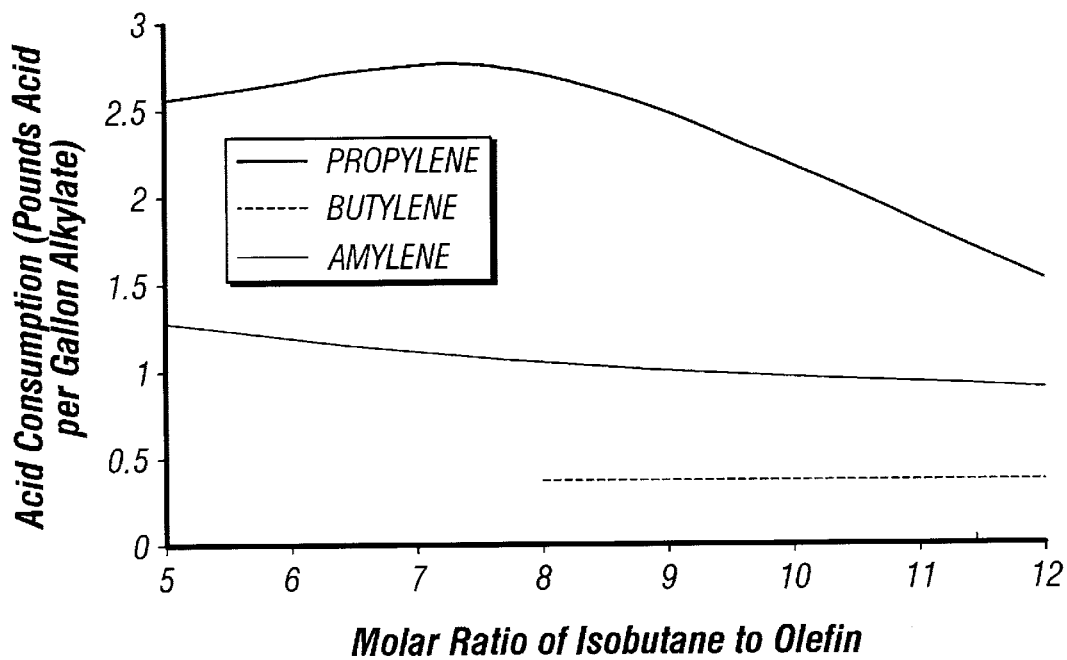
FIG. 22 is a graph showing the relationship between pounds acid consumption per gallons of net alkylate product produced and the isobutane to olefin ratio.
Figure 23:
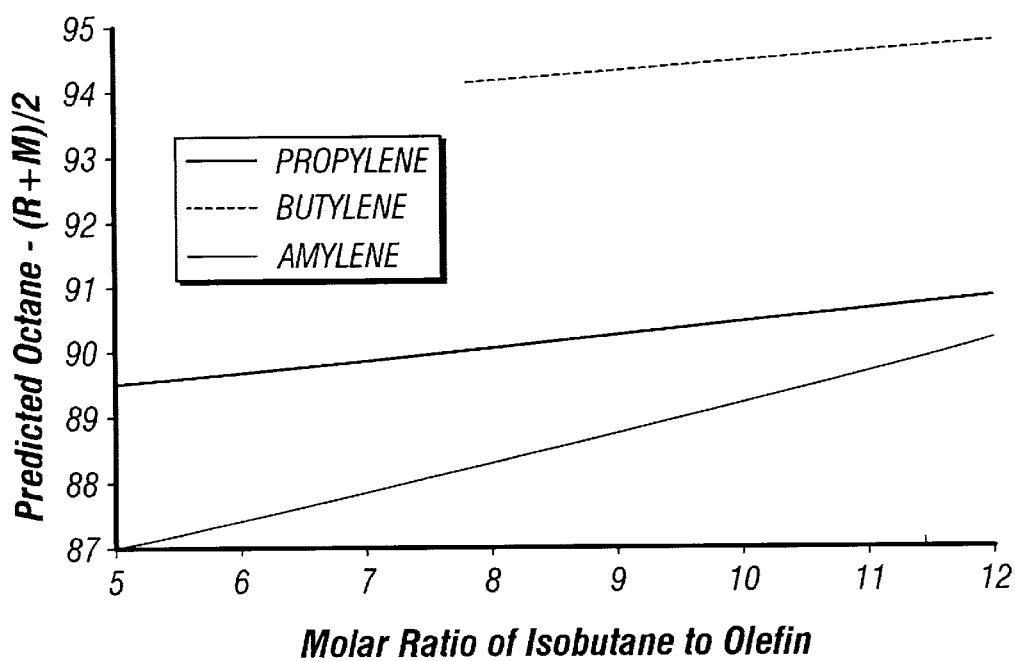
FIG. 23 is a graph showing the relationship between octane number of the alkylate product produced and isobutane to olefin ratio.

FIGS. 22 and 23 are graphs which show the effect of isobutane/olefin ration on acid consumption and alkylate octane, respectively.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled the art to which this invention pertains.

We claim:
1. A process for alkylating comprising:
   (a) contacting an olefin mixture comprising $C_3$ and iso-$C_5$ olefins with an isoparaffin in the presence of an acid catalyst under conditions effective to produce a spent acid catalyst and an alkylate product; wherein the mole ratio of $C_3$ olefins to iso-$C_5$ olefins is in the range of about 45:55 to about 95:5.

2. The process of claim 1 further comprising:
   (b) contacting an olefin mixture comprising at least one olefin selected from the group of olefins consisting of $C_4$ and $C_5$ olefins that are substantially free of $C_3$ olefins, with an isoparaffin, in the presence of the spent acid catalyst of step (a) to produce a second alkylate product.

3. The process of claim 1 wherein the isoparaffin comprises isobutane.

4. The process of claim 3 wherein the ratio of $C_3$ olefins to iso-$C_5$ olefins is in the range of about 65:35 to about 90:10.

5. The process of claim 3 wherein the ration of $C_3$ olefins to iso-$C_5$ olefins is in the range of about 70:30 to about 90:10.

6. The process of claim 3 wherein the ratio of $C_3$ olefins to iso-$C_5$ olefins is in the range of about 75:25 to about 90:10.

7. The process of claim 6 wherein the isoparaffin further comprises isopentane.

8. The process of claim 1 wherein the isoparaffin comprises isobutane, the ratio of $C_3$ olefins to iso-$C_5$ olefins is in the range of about 45:55 to about 85:15, and the catalyst comprises sulfuric acid.

9. A process for alkylating comprising:
   (a) contacting an olefin mixture comprising $C_3$ olefins that are substantially free of $C_4$ and $C_5$ olefins, with an isoparaffin in the presence of an acid catalyst, to produce a first alkylate product and a first spent acid catalyst;
   (b) contacting an olefin mixture comprising $C_4$ or $C_5$ olefins that are substantially free of $C_3$ olefins, with an isoparaffin, in the presence of the spent acid catalyst of step (a) to produce a second alkylate product and a second spent acid catalyst.

10. The process of claim 9 wherein the olefin mixture of step (a) comprises at least 75 weight percent $C_3$ olefins, and wherein the olefin mixture of step (b) comprises at least 75 weight percent $C_4$ or $C_5$ olefins.

11. The process of claim 10 wherein the isoparaffin in step (a) and step (b) comprises isobutane, and the acidity of the spent acid catalyst of step (a) is at least 88%.

12. The process of claim 11 wherein olefin mixture of step (b) comprises at least 75 weight percent $C_4$ olefins and less than 25 weight percent $C_3$ or $C_5$ olefins.

13. The process of claim 11 further comprising:
(c) contacting an olefin mixture of amylenes that are substantially free of $C_3$ or $C_4$ olefins, with an isoparaffin, in the presence of the spent acid catalyst of step (b) to produce a third alkylate product.

14. The process of claim 11 wherein olefin mixture of step (b) comprises at least 75 weight percent $C_5$ olefins and less than 25 weight percent $C_3$ or $C_4$ olefins.

15. A process for alkylating comprising:
(a) contacting an olefin mixture comprising $C_3$ olefins that are substantially free of $C_5$ olefins, with an isoparaffin in the presence of an acid catalyst, to produce a first alkylate product and a first spent catalyst;
(b) contacting an olefin mixture comprising $C_5$ olefins that are substantially free of $C_3$ olefins, with an isoparaffin, in the presence of the spent acid catalyst of step (a) to produce a second alkylate product and a second spent catalyst.

16. The process of claim 15 wherein the contacting of step (a) is within a first reaction zone, the contacting of step (b) is within a second reaction zone, where the process further comprises:
(c) recovering in a settler at least a portion of the first spent acid catalyst and at least a portion of the second spent acid catalyst to form a recovered spent acid catalyst; and
(d) recycling at least a portion of the recovered spent acid catalyst to step (a) and at least a portion of the recovered spent acid catalyst to step (b).

17. The process of claim 15 wherein the olefin mixture of step (a) further comprises butylenes, and the olefin mixture of step (b) further comprises butylenes.

18. The process of claim 16 wherein the contacting of step (a) is within a first reaction zone, the contacting of step (b) is within a second reaction zone, where the process further comprises:
(c) recovering in a settler at least a portion of the first spent acid catalyst and at least a portion of the second spent acid catalyst to form a recovered spent acid catalyst; and
(d) recycling at least a portion of the recovered spent acid catalyst to step (a) and at least a portion of the recovered spent acid catalyst to step (b).

19. A process for alkylating comprising:
(a) contacting $C_3$ olefins that are substantially free of $C_4$ and $C_5$ olefins, with an isoparaffin in the presence of an acid catalyst, to produce a first alkylate product and a first spent acid;
(b) contacting $C_4$ olefins that are substantially free of $C_3$ and $C_5$ olefins, with an isoparaffin in the presence of the spent acid catalyst of step (a), to produce a second alkylate product and a second spent acid; and
(c) contacting $C_5$ olefins that are substantially free of $C_3$ and $C_4$ olefins, with an isoparaffin the presence of the spent acid catalyst of step (b), to produce a third alkylate product and a third spent acid.

20. A process for alkylating comprising:
(a) contacting $C_3$ olefins that are substantially free of $C_4$ olefins, with an isoparaffin in the presence of an acid catalyst, to produce a first alkylate product;
(b) contacting $C_4$ olefins that are substantially free of $C_3$ olefins, with an isoparaffin in the presence of an acid catalyst, to produce a second alkylate product;
(c) recovering the acid catalyst of step (a) and the acid catalyst of step (b) to form a recovered acid catalyst product; and
(d) recycling a portion of the recovered acid catalyst product back to step (a) to comprise the acid catalyst in step (a), and a portion of the recovered acid catalyst stream back to step (b) to comprise the acid catalyst in step (b).

21. The process of claim 1 further comprising:
(b) contacting an olefin mixture that is substantially free of $C_3$ olefins with an isoparaffin in the presence of the spent acid catalyst of step (a) to produce a second alkylate product, wherein the olefin mixture comprises at least one olefin selected from the group consisting of $C_4$ and $C_5$ olefins.

* * * * *